United States Patent
Baudner et al.

(10) Patent No.: US 10,603,369 B2
(45) Date of Patent: *Mar. 31, 2020

(54) COMBINATION VACCINES WITH LOWER DOSES OF ANTIGEN AND/OR ADJUVANT

(71) Applicant: GlaxoSmithKline Biologicals SA, Rixensart (BE)

(72) Inventors: Barbara Baudner, Siena (IT); David Skibinski, Singapore (SG); Manmohan Singh, Cambridge, MA (US); Derek O'Hagan, Cambridge, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 64 days.

This patent is subject to a terminal disclaimer.

(21) Appl. No.: 15/887,203

(22) Filed: Feb. 2, 2018

(65) Prior Publication Data

US 2018/0169204 A1 Jun. 21, 2018

Related U.S. Application Data

(63) Continuation of application No. 14/002,700, filed as application No. PCT/IB2012/050989 on Mar. 2, 2012, now abandoned.

(60) Provisional application No. 61/565,980, filed on Dec. 1, 2011, provisional application No. 61/448,226, filed on Mar. 2, 2011.

(51) Int. Cl.
| | |
|---|---|
| *A61K 39/00* | (2006.01) |
| *A61K 31/4375* | (2006.01) |
| *A61K 31/66* | (2006.01) |
| *A61K 33/06* | (2006.01) |
| *A61K 39/39* | (2006.01) |
| *A61K 39/12* | (2006.01) |
| *A61K 39/102* | (2006.01) |
| *A61K 39/116* | (2006.01) |
| *A61K 39/295* | (2006.01) |

(52) U.S. Cl.
CPC ...... *A61K 39/0018* (2013.01); *A61K 31/4375* (2013.01); *A61K 31/66* (2013.01); *A61K 33/06* (2013.01); *A61K 39/102* (2013.01); *A61K 39/116* (2013.01); *A61K 39/12* (2013.01); *A61K 39/295* (2013.01); *A61K 39/39* (2013.01); *A61K 2039/545* (2013.01); *A61K 2039/55505* (2013.01); *A61K 2039/55555* (2013.01); *A61K 2039/55566* (2013.01); *A61K 2039/70* (2013.01); *C12N 2730/10134* (2013.01); *C12N 2770/32634* (2013.01); *Y02A 50/466* (2018.01)

(58) Field of Classification Search
None
See application file for complete search history.

(56) References Cited

U.S. PATENT DOCUMENTS

| | | | |
|---|---|---|---|
| 4,666,886 A | 5/1987 | Baschang et al. | |
| 5,059,258 A | 10/1991 | Wefers et al. | |
| 5,936,076 A | 8/1999 | Higa et al. | |
| 6,699,474 B1 | 3/2004 | Cerny | |
| 7,115,592 B2 | 10/2006 | Balzarini et al. | |
| 7,220,545 B2 | 5/2007 | Binz et al. | |
| 7,309,494 B2 | 12/2007 | Corvaia et al. | |
| 7,488,490 B2 | 2/2009 | Davis et al. | |
| 7,691,877 B2 | 4/2010 | Jones et al. | |
| 7,771,726 B2 | 8/2010 | Tsuji et al. | |
| 8,222,257 B2 | 7/2012 | Hostetler et al. | |
| 8,275,711 B2 | 9/2012 | Jackowski et al. | |
| 8,367,670 B2 | 2/2013 | Desai et al. | |
| 8,466,167 B2 | 6/2013 | Wu et al. | |
| 9,045,470 B2 | 6/2015 | Wu et al. | |
| 9,315,530 B2 | 4/2016 | Singh et al. | |
| 9,375,471 B2 | 6/2016 | Baudner et al. | |
| 2004/0202668 A1 | 10/2004 | Boutriau et al. | |
| 2008/0008682 A1 | 1/2008 | Chong et al. | |
| 2009/0099216 A1 | 4/2009 | Millichip et al. | |
| 2009/0105212 A1 | 4/2009 | Isobe et al. | |
| 2009/0118263 A1 | 5/2009 | Hashimoto et al. | |
| 2009/0143400 A1 | 6/2009 | McInally et al. | |
| 2009/0192153 A1 | 7/2009 | Hashimoto et al. | |
| 2009/0208523 A1 | 8/2009 | Broeker | |
| 2009/0208526 A1 | 8/2009 | Contorni | |
| 2009/0221631 A1 | 9/2009 | Jones et al. | |
| 2009/0232844 A1 | 9/2009 | Sutton et al. | |
| 2010/0056031 A1 | 3/2010 | Chiu et al. | |
| 2011/0028715 A1 | 2/2011 | Isobe et al. | |
| 2011/0180430 A1 | 7/2011 | Rappuoli et al. | |
| 2012/0177681 A1 | 7/2012 | Singh et al. | |
| 2012/0237546 A1 | 9/2012 | Singh et al. | |
| 2013/0122042 A1 | 5/2013 | Otten et al. | |
| 2013/0236492 A1 | 9/2013 | Baudner et al. | |
| 2013/0330840 A1 | 12/2013 | Skibinski et al. | |
| 2014/0363461 A1 | 12/2014 | Bagnoli et al. | |
| 2015/0030630 A1 | 1/2015 | Jain et al. | |
| 2015/0125475 A1 | 5/2015 | Dodd et al. | |
| 2015/0132339 A1 | 5/2015 | Bufali et al. | |
| 2015/0190493 A1 | 7/2015 | Baudner et al. | |
| 2015/0258190 A1 | 9/2015 | Grandi | |

FOREIGN PATENT DOCUMENTS

| | | |
|---|---|---|
| CN | 1130226 C | 12/2003 |
| CN | 101522217 A | 9/2009 |

(Continued)

OTHER PUBLICATIONS

Abarca, "Reduced-Antigen Combined Diphtheria-Tetanus-Acellular Pertussis Vaccine (Boostrix™) A Viewpoint by Katia Abarca," Drugs, vol. 63, No. 13, Jan. 1, 2003, pp. 1415-1416, XP008025045.

(Continued)

*Primary Examiner* — Patricia Duffy
(74) *Attorney, Agent, or Firm* — Birch, Stewart, Kolasch & Birch, LLP

(57) ABSTRACT

Combination vaccine compositions as well as methods for their manufacture have a relatively low amount of antigen and/or a relatively low amount of aluminium, but they can nevertheless have immunogenicity which is comparable to combination vaccines with a relatively high amount of antigen and/or a relatively high amount of aluminium. Aluminium-free combination vaccine compositions are also provided e.g. compositions which are adjuvanted with an oil-in-water emulsion adjuvant.

15 Claims, No Drawings

(56) References Cited

FOREIGN PATENT DOCUMENTS

| | | |
|---|---|---|
| JP | 2007-529503 A | 10/2007 |
| WO | WO 93/18150 A1 | 9/1993 |
| WO | WO 95/27787 A1 | 10/1995 |
| WO | WO 96/01272 A1 | 1/1996 |
| WO | WO 96/01273 A1 | 1/1996 |
| WO | WO 96/16046 A2 | 5/1996 |
| WO | WO 97/25429 A1 | 7/1997 |
| WO | WO 98/19702 A1 | 5/1998 |
| WO | WO 00/37494 A2 | 6/2000 |
| WO | WO 02/02606 A2 | 1/2002 |
| WO | WO 03/010317 A1 | 2/2003 |
| WO | WO 03/049762 A2 | 6/2003 |
| WO | WO 03/097091 A2 | 11/2003 |
| WO | WO 03/105769 A2 | 12/2003 |
| WO | WO 2004/032958 A1 | 4/2004 |
| WO | WO 2004/111064 A1 | 12/2004 |
| WO | WO 2005/002619 A2 | 1/2005 |
| WO | WO 2005/084306 A2 | 9/2005 |
| WO | WO 2005/089794 A2 | 9/2005 |
| WO | WO 2005/102049 A1 | 11/2005 |
| WO | WO 2006/089264 A2 | 8/2006 |
| WO | WO 2006/091517 A2 | 8/2006 |
| WO | WO 2006/138004 A2 | 12/2006 |
| WO | WO 2007/000322 A1 | 1/2007 |
| WO | WO 2007/034173 A1 | 3/2007 |
| WO | WO 2007/034917 A1 | 3/2007 |
| WO | WO 2007/040840 A2 | 4/2007 |
| WO | WO 2007/060548 A2 | 5/2007 |
| WO | WO 2007/093901 A1 | 8/2007 |
| WO | WO 2007/109813 A1 | 9/2007 |
| WO | WO 2007/110700 A2 | 10/2007 |
| WO | WO 2008/004948 A1 | 1/2008 |
| WO | WO 2008/005555 A1 | 1/2008 |
| WO | WO 2008/020328 A2 | 2/2008 |
| WO | WO 2008/020330 A2 | 2/2008 |
| WO | WO 2008/047174 A1 | 4/2008 |
| WO | WO 2008/047249 A2 | 4/2008 |
| WO | WO 2008/101867 A1 | 8/2008 |
| WO | WO 2008/114817 A1 | 9/2008 |
| WO | WO 2008/135791 A1 | 11/2008 |
| WO | WO 2009/019553 A2 | 2/2009 |
| WO | WO 2009/050586 A1 | 4/2009 |
| WO | WO 2009/067081 A1 | 5/2009 |
| WO | WO 2009/081172 A1 | 7/2009 |
| WO | WO 2009/111337 A1 | 9/2009 |
| WO | WO 2009/118296 A2 | 10/2009 |
| WO | WO 2010/003009 A2 | 1/2010 |
| WO | WO 2010/014913 A1 | 2/2010 |
| WO | WO 2010/067201 A2 | 6/2010 |
| WO | WO 2010/077613 A1 | 7/2010 |
| WO | WO 2010/094663 A1 | 8/2010 |
| WO | WO 2010/119343 A2 | 10/2010 |
| WO | WO 2010/140119 A1 | 12/2010 |
| WO | WO 2010/144734 A1 | 12/2010 |
| WO | WO 2011/024072 A2 | 3/2011 |
| WO | WO 2011/027222 A2 | 3/2011 |
| WO | WO 2011/057267 A1 | 5/2011 |
| WO | WO 2011/119759 A1 | 9/2011 |
| WO | WO 2012/031140 A1 | 3/2012 |
| WO | WO 2012/117377 A1 | 9/2012 |

OTHER PUBLICATIONS

Banus et al. "The Role of Toll-like Receptor-4 in Pertussis Vaccine-induced Immunity," BMC Immunololgy, vol. 9, No. 21, May 22, 2008, 15 pages, XP021033213.

Barnett et al., "The Ability of an Oligomeric Human Immunodeficiency Virus Type 1 (HIV-1) Envelope Antigen to Elicit Neutralizing Antibodies against Primary HIV-1 Isolates is Improved Following Partial Deletion of the Second Hypervariable Region," J. Virol, vol. 75, No. 12, Jun. 2001, pp. 5526-5540.

Billaudelle et al., "Trippelvaccin Utan Aluminium-'carrier,'" Nord. Med., vol. 68, No. 42, Oct. 18, 1962, pp. 1339-1340, XP009159265.

Bortolatto et al., "Toll-like Receptor 4 Agonists Adsorbed to Aluminium Hydroxide Adjuvant Attenuate Ovalbumin-specific Allergic Airway Disease: Role of MyD88 Adaptor Molecule and Interleukin-12/interferon-γ Axis," Clin. Exper. Aller., vol. 38, No. 10, 2008, pp. 1668-1679.

Brewer, "(How) Do Aluminium Adjuvants Work?" Immunol. Lett. vol. 102, No. 1, Jan. 15, 2006 (Available online Aug. 30, 2005), pp. 10-15, XP024999104.

Burrell et al., "Stability of Aluminium-containing Adjuvants to Autoclaving," Vaccine, vol. 17, 1999, pp. 2599-2603.

Cassone et al., "Opportunistic Fungi and Fungal Infections: The Challenge of a Single, General Antifungal Vaccine," Expert Rev. Vaccines, vol. 5, No. 6, 2006, pp. 859-867.

CDC, "Notice to Readers Availability of New Rabies Vaccine for Human Use," MMWR Weekly Report, vol. 47, No. 1, Jan. 16, 1998, 3 pages.

Chang et al., "Degree of Antigen Adsorption in the Vaccine or Interstitial Fluid and Its Effect on the Antibody Response in Rabbits," Vaccine, vol. 19, 2001, pp. 2884-2889.

Clausi et al., "Influence of Particle Size and Antigen Binding on Effectiveness of Aluminum Salt Adjuvants in a Model Lysozyme Vaccine," J. Pharm. Sci., vol. 97, No. 12, Dec. 2008, pp. 5252-5262.

Cooper et al., "CPG 7909, An Immunostimulatory TLR9 Agonist Oligodeoxynucleotide, as Adjuvant to Engerix-B® HBV Vaccine in Healthy Adults: A Double-Blind Phase I/II Study," J. Clin. Immun., vol. 24, No. 6, Nov. 2004, pp. 693-701.

Covacci et al., "Molecular Characterization of the 128-kDa Immunodominant Antigen of Helicobacter Pylori Associated with Cytotoxicity and Duodenal Ulcer," Proc. Natl. Acad. Sci. USA, vol. 90, Jun. 1993, pp. 5791-5795.

Covacci et al., "Tyrosine-phosphorylated Bacterial Proteins: Trojan Horses for the Host Cell," J. Exp. Med., vol. 191, No. 4, Feb. 21, 2000, pp. 587-592.

Dasari et al., "Recombinant Glycoprotein B Vaccine Formulation with Toll-like Receptor 9 Agonist and Immune-stimulating Complex Induces Specific Immunity against Multiple Strains of Cytomeagalovirus," J. Gen. Virol., vol. 92, 2011, pp. 1021-1031.

Davis et al., "CpG DNA is a Potent Enhancer of Specific Immunity in Mice Immunized with Recombinant Hepatitis B Surface Antigen," J. Immunol., vol. 160, 1998, pp. 870-876.

De Libero et al., "Recognition of Lipid Antigens by T Cells," Nature Reviews Immunology, vol. 5, Jun. 2005, pp. 485-496.

Earl et al., "Immunogenicity and Protective Efficacy of Oligomeric Human Immunodeficiency Virus Type 1 gp140," J. Virol., vol. 75, No. 2, Jan. 2001, pp. 645-653.

Evans Jr. et al, "Identification of Four New Prokaryotic Bacterioferritins, from Helicobacter Pylori, Anabaena Variabilis, Bacillus Subtilis and Treponema Pallidum, by Analysis of Gene Sequences," Gene, vol. 153, 1995, pp. 123-127.

Garçon et al., "Development and Evaluation of AS04, A Novel and Improved Adjuvant System Containing MPL and Aluminum Salt," Immunopotentiators in Modern Vaccines, Jan. 1, 2006, pp. 161-177, XP009140248.

Gennaro, "Remington: The Science and Practice of Pharmacy," Table of Contents, 20th Edition, ISBN: 0683306472, 2000, 4 pages.

Geurtsen et al., "Lipopolysaccharide Analogs Improve Efficacy of Acellular Pertussis Vaccine and Reduce Type I Hypersensitivity in Mice," Clin. Vaccine Immunol., vol. 14, No. 7, Jul. 1, 2007, pp. 821-829, XP055060805.

Giuliani et al., "A Universal Vaccine for Serogroup B Meningococcus," Proc. Natl. Acad. Sci. USA, vol. 103, No. 29, Jul. 18, 2006, pp. 10834-10839.

Goff et al., "Effects of Lipid Chain Lengths in α-Galactosylceramides on Cytokine Release by Natural Killer T Cells," J. Am. Chem. Soc., vol. 126, No. 42, 2004 (Published online Oct. 2, 2004), pp. 13602-13603.

Gröndahl-Yli-Hannuksela et al., "Gene Polymorphism in Toll-like Receptor 4: Effect on Antibody Production and Persistence after Acellular Pertussis Vaccination during Adolescence," J. Infect. Dis., vol. 205, No. 8, Apr. 15, 2012 (Electronically published Mar. 1, 2012), pp. 1214-1219, XP002696252.

(56) References Cited

OTHER PUBLICATIONS

Hancock et al."Adjuvants Recognized by Toll-like Receptors Inhibit the Induction of Polarized Type 2 T Cell Responses by Natural Attachment (G) Protein of Respiratory Syncytial Virus," Vaccine, vol. 21, 2003, pp. 4348-4358.
Harper et al., "Efficacy of a Bivalent L1 Virus-like Particle Vaccine in Prevention of Infection with Human Papillomavirus Types 16 and 18 in Young Women: A Randomised Controlled Trial," Lancet, vol. 364, Nov. 13, 2004, pp. 1757-1765.
Hashiro et al., "Rapid and Efficient Induction of an Endogenous Cell Signaling Event by Subcellular Targeting of a Synthetic Ligand," JACS, vol. 131, No. 38, 2009 (Web Publication Date Sep. 2, 2009), pp. 13568-13569.
Hem et al., "Relationship between Physical and Chemical Properties of Aluminum-containing Adjuvants and Immunopotentiation," Expert Review Vaccines, vol. 6, No. 5, 2007 (Oct. 1, 2007), pp. 685-698, XP009143527.
Hem et al., "Structure and Properties of Aluminum-Containing Adjuvants," Vaccine Design: The Subunit and Adjuvant Approach, Chapter 9, Plenum Press, New York, Jan. 1, 1995, pp. 249-276, XP0001053762.
Hocková et al., "5-Substituted-2,4-diamino-6-[2-(phosphonomethoxy)ethoxy]pyrimidines-Acyclic Nucleoside Phosphonate Analogues with Antiviral Activity," J. Med. Chem., vol. 46, No. 23, 2003 (Published on Web Oct. 15, 2003), pp. 5064-5073.
International Search Report (form PCT/ISA/210), dated Aug. 14, 2012, for International Application No. PCT/IB2012/050989.
Iyer et al., "Mechanism of Adsorption of Hepatitis B Surface Antigen by Aluminum Hydroxide Adjuvant," Vaccine, vol. 22, 2004, pp. 1475-1479.
Keitel et al., "Increasing Doses of Purified Influenza Virus Hemagglutinin and Subvirion Vaccines Enhance Antibody Responses in the Elderly," Clin. Diagn. Lab. Immunol., vol. 3, No. 5, Sep. 1996, 507-510.
Leroux-Roels, "Unmet Needs in Modern Vaccinology Adjuvants to Improve the Immune Response," Vaccine, vol. 285, 2010, pp. C25-C36.
Levesque et al., "Mechanism of Adsorption of Three Recombinant *Streptococcus pneumoniae* (Sp) Vaccine Antigens by an Aluminum Adjuvant," Human Vaccines, vol. 1, No. 2, Mar./Apr. 2005, pp. 70-73.
Mansour et al., "Improved Efficacy of a Licensed Acellular Pertussis Vaccine, Reformulated in an Adjuvant Emulsion of Liposomes in Oil, in a Murine Model," Clin. Vaccine Immunol., vol. 14, No. 10, Oct. 2007 (Published ahead of print Aug. 22, 2007), pp. 1381-1383, XP055025140.
Marchetti et al., "Protection against Helicobacter Pylori Infection in Mice by Intragastric Vaccination with H. Pylori Antigens is Achieved Using a Non-toxic Mutant of *E. coli* Heat-labile Enterotoxin (LT) as Adjuvant," Vaccine, vol. 16, No. 1, 1998, pp. 33-37.
Méndez et al., "Potentiation of the Immune Response to Non-adsorbed Antigens by Aluminum-containing Adjuvants," Vaccine, vol. 25, 2007 (Available online Sep. 25, 2006), pp. 825-833.
Morefield et al., "Effect of Phosphorylation of Ovalbumin on Adsorption by Aluminum-containing Adjuvants and Elution upon Exposure to Interstitial Fluid," Vaccine, vol. 23, 2005 (Available online Oct. 30, 2004), pp. 1502-1506.
Munoz, "Pertussis in Infants, Children, and Adolescents: Diagnosis, Treatment, and Prevention," Seminars in Pediatric Infectious Diseases, vol. 17, 2006, pp. 14-19.
Nencioni et al., "Properties of Pertussis Toxin Mutant PT-9K/129G after Formaldehyde Treatment," Infect. Immun., vol. 59, No. 2, Feb. 1991, pp. 625-630.
Oki et al., The Clinical Implication and Molecular Mechanism of Preferential IL-4 production by Modified Glycolipid-stimulated NKT Cells, J. Clin. Investig., vol. 113, No. 11, Jun. 2004, pp. 1631-1640.

Powell et al., "Vaccine Design, The Subunit and Adjuvant Approach," Pharmaceutical Biotechnology, vol. 6, Table of Contents, ISBN: 030644867X, 1995, 23 pages.
Racke et al., "PTX Cruiser: Driving Autoimmunity via TLR4," Trends Immunol., vol. 26, No. 6, Jun. 1, 2005 (Available online Apr. 8, 2005), pp. 289-291, XP027724307.
Rappuoli et al., "Towards Third-generation Whooping Cough Vaccines," TIBTECH, vol. 9, Jul. 1991, pp. 232-238.
Response to Notice of Non-Compliant Amendment, dated Jul. 21, 2014, for U.S. Appl. No. 13/790,948, filed Mar. 8, 2013.
Response to U.S. Final Action, dated Jan. 8, 2015, for U.S. Appl. No. 13/394,036, filed Sep. 1, 2010.
Response to U.S. Final Office Action, dated Dec. 4, 2014, for U.S. Appl. No. 13/394,036, filed Sep. 1, 2010.
Rosenberg et al., "TLR Reporter Cell Lines for Screening TLR Agonists and Antagonists," Meeting Abstract, J. Immunol., vol. 184, No. 136, 2010, 1 page.
Scheifele et al., "Can Reductions in Diphtheria Toxoid or Aluminum Content Reduce the Reactogenicity of Booster Doses of DPT Vaccine?" Immunology and Infectious Diseases, vol. 5, No. 1, 1995 (Mar. 1, 1995), pp. 73-77 (8 pages total), XP000891884.
Shi et al., "Change in the Degree of Adsorption of Proteins by Aluminum-containing Adjuvants Following Exposure to Interstitial Fluid: Freshly Prepared and Aged Model Vaccines," Vaccine, vol. 20, 2002, pp. 80-85.
Singh et al., "A Preliminary Evaluation of Alternative Adjuvants to Alum using a Range of Established and New Generation Vaccine Antigens," Vaccine, vol. 24, No. 10, 2006 (Available online Oct. 6, 2005), pp. 1680-1686 (8 pages total), XP025151148.
Steinhagen et al., "TLR-based Immune Adjuvants," Vaccine, vol. 29, No. 17, Apr. 12, 2011, pp. 3341-3355 (33 pages total), XP028380413.
Sugai et al., "A CpG-containing Oligodeoxynucleotide as an Efficient Adjuvant Counterbalancing the Th1/Th2 Immune Response in Diphtheria-tetanus-pertussis Vaccine," Vaccine, vol. 23, Nos. 46-47, 2005 (Available online Jun. 21, 2005), pp. 5450-5456, XP27651991.
Telford et al., "Gene Structure of the Helicobacter Pylori Cytotoxin and Evidence of its Key Role in Gastric Disease," J. Exp. Med., vol. 179, May 1994, pp. 1653-1658.
Treanor et al., "Evaluation of a Recombinant Hemagglutinin Expressed in Insect Cells as an Influenza Vaccine in Young . . . ," J. Infect. Dis., vol. 173, 1996 (Presented in part: 33rd Annual Meeting, Infectious Diseases Society of America, San Francisco, USA, Sep. 1995), pp. 1467-1470.
Tummuru et al., "Cloning and Expression of a High-molecular-mass Major Antigen of Helicobacter Pylori: Evidence of Linkage to Cytotoxin Production," Infect. Immun., vol. 61, No. 5, May 1993, pp. 1799-1809.
U.S. Advisory Action, dated Dec. 11, 2014, for U.S. Appl. No. 13/394,036.
U.S. Final Office Action, dated May 28, 2015, for U.S. Appl. No. 13/790,948.
U.S. Final Office Action, dated Sep. 8, 2014, for U.S. Appl. No. 13/394,036.
U.S. Office Action, dated Aug. 14, 2015, for U.S. Appl. No. 13/394,036.
Van Duin, "Triggering TLR Signaling in Vaccination," Trends Immunol., vol. 27, No. 1, Jan. 1, 2006 (Available online Nov. 23, 2005), pp. 49-55, XP028058539.
Vecchi et al., "Aluminum Adjuvant Dose Guidelines in Vaccine Formulation for Preclinical Evaluations," J. Pharm. Sci., vol. 101, No. 1, Jan. 2012 (Published online Sep. 14, 2011), pp. 17-20, XP002675877.
Vergara et al., "Reduced-antigen-content-diphtheria-tetanus-acellular-pertussis and Inactivated Polio Vaccine as a Booster for Adolescents 10 to 14 years of Age," Eur. J. Pediatr., vol. 164, 2005 (Published online Mar. 22, 2005), pp. 377-382.
Wack et al, "Combination Adjuvants for the Induction of Potent, Long-lasting Antibody and T-cell Responses to Influenza Vaccine in Mice," Vaccine, vol. 26, 2008 (Available online Dec. 26, 2007), pp. 552-561.
Wendorf et al, "A Comparison of Anionic Nanoparticles and Microparticles as Vaccine Delivery Systems," Hum. Vaccine, vol. 4, No. 1, Jan. 1, 2008, pp. 44-49 (7 pages total), XP001539000.

(56) References Cited

OTHER PUBLICATIONS

Weston et al., "Safety and Immunogenicity of a Tetanus Toxoid, Reduced Diphtheria Toxoid, and Acellular Pertussis Vaccine when Co-administered with Influenza Vaccine in Adults," Human Vaccines, vol. 5, No. 12, 2009 (Published online Dec. 1, 2009), pp. 858-866 (10 pages total).

Written Opinion of the International Searching Authority and International Search Report (forms PCT/ISA/237 and PCT/ISA/210), dated Feb. 10, 2014, for International Application No. PCT/EP2013/054672.

Written Opinion of the International Searching Authority and International Search Report (forms PCT/ISA/237 and PCT/ISA/210), dated Feb. 18, 2011, for International Application No. PCT/IB2010/002386.

Wu et al., "Rational Design of Small Molecules as Vaccine Adjuvants," Sci. Transl. Med., vol. 6, No. 263, Nov. 19, 2014, pp. 1-12 (13 pages total).

Yang et al., "The C-Glycoside Analogue of the Immunostimulant α-Galactosylceramide (KRN7000): Synthesis and Striking Enhancement of Activity," Angew Chem. Int. Ed., vol. 43, 2004, pp. 3818-3822.

Zhang et al., "Expression, Purification, and Characterization of Recombinant HIV gp140. The gp41 Ectodomain of HIV or Simian Immunodeficiency Virus is Sufficient to Maintain . . . ," J. Biol. Chem., vol. 276, No. 43, Oct. 26, 2001 (Published JBC Papers in Press, Aug. 20, 2001), pp. 39577-39585.

COMBINATION VACCINES WITH LOWER DOSES OF ANTIGEN AND/OR ADJUVANT

CROSS-REFERENCE TO RELATED APPLICATIONS

This application is a Continuation of co-pending U.S. application Ser. No. 14/002,700, filed on Jan. 10, 2014, which is the U.S. National Phase of International Application No. PCT/IB2012/050989, filed on Mar. 2, 2012 and published in English; which claims priority to U.S. Provisional Application No. 61/448,226, filed on Mar. 2, 2011 and U.S. Provisional Application No. 61/565,980, filed on Dec. 1, 2011. The teachings of the above applications are incorporated herein in their entirety by reference.

TECHNICAL FIELD

This invention is in the field of combination vaccines i.e. vaccines containing mixed immunogens from more than one pathogen, such that administration of the vaccine can simultaneously immunize a subject against more than one pathogen.

BACKGROUND ART

Vaccines containing antigens from more than one pathogenic organism within a single dose are known as "multivalent" or "combination" vaccines. Various combination vaccines have been approved for human use in the EU and the USA, including trivalent vaccines for protecting against diphtheria, tetanus and pertussis ("DTP" vaccines) and trivalent vaccines for protecting against measles, mumps and rubella ("MMR" vaccines). Combination vaccines offer patients the advantage of receiving a reduced number of injections, which can lead to the clinical advantage of increased compliance (e.g. see chapter 29 of reference 1), particularly for pediatric vaccination.

Current combination vaccines can include relatively high amounts of aluminium salts as adjuvants which causes concern to some patient pressure groups despite empirical safety studies [2,3]. For instance, the aluminium levels in known combination vaccines are as follows (see also Table A below):

| Trade name | Antigens | $Al^{+++}$ content per unit dose |
| --- | --- | --- |
| Pediacel | D-T-Pa-Hib-IPV | 0.33 mg |
| Pediarix | D-T-Pa-HBV-IPV | ≤0.85 mg |
| Pentacel | D-T-Pa-Hib-IPV | 0.33 mg |
| Tritanrix-HepB | D-T-Pw-HBV | 0.63 mg |
| Quinvaxem | D-T-Pw-Hib-HBV | 0.3 mg |
| Hexavac | D-T-Pa-IPV-Hib-HBV | 0.3 mg |
| Boostrix (USA) | D-T-Pa | ≤0.39 mg |

A vaccine with lower levels of aluminium would be helpful for some patient groups, and it is an object of the present invention to provide such vaccines, ideally without loss of vaccine potency. Another drawback with current vaccines is that they require relatively high amounts of antigen, whereas various documents show that protective effects might be achieved with lower amounts of antigen e.g. reference 4 shows that the amount of Hib antigen can be halved in a D-T-Pw-Hib vaccine without loss of immunological response, and reference 5 argues that a reduced WV dose can be used while maintaining an adequate level of protection against polio. It is an object of the present invention to provide further vaccines with reduced amounts of antigen, ideally without loss of immunoprotective effect.

SUMMARY OF THE INVENTION

The invention provides a variety of combination vaccine compositions as well as methods for their manufacture. Typically the compositions have a relatively low amount of antigen and/or a relatively low amount of aluminium, but they can nevertheless have immunogenicity which is comparable to combination vaccines with a relatively high amount of antigen and/or a relatively high amount of aluminium. Aluminium-free combination vaccine compositions are also provided e.g. compositions which are adjuvanted with an oil-in-water emulsion adjuvant.

In a first embodiment the invention provides an immunogenic composition in a unit dose form for administration to a patient comprising (i) a diphtheria toxoid, a tetanus toxoid, and a pertussis toxoid, and (ii) an aluminium salt adjuvant, wherein the amount of $Al^{+++}$ in the unit dose is less than 0.2 mg.

The invention also provides an immunogenic composition comprising (i) a diphtheria toxoid, a tetanus toxoid, and a pertussis toxoid and (ii) an aluminium salt adjuvant, wherein the concentration of $Al^{+++}$ is less than 0.4 mg/ml.

In a second embodiment the invention provides an immunogenic composition comprising (i) an aluminium salt adjuvant and (ii) a low dose of each of a diphtheria toxoid, a tetanus toxoid, and a pertussis toxoid.

In a third embodiment the invention provides an immunogenic composition in a unit dose form for administration to a patient comprising (i) a low dose of each of a diphtheria toxoid, a tetanus toxoid, and a pertussis toxoid, and (ii) an aluminium salt adjuvant, wherein the amount of $Al^{+++}$ in the unit dose is less than 0.2 mg.

The invention also provides an immunogenic composition comprising (i) a low dose of each of a diphtheria toxoid, a tetanus toxoid, and a pertussis toxoid and (ii) an aluminium salt adjuvant, wherein the concentration of $Al^{+++}$ is less than 0.4 mg/ml.

In a fourth embodiment the invention provides an immunogenic composition comprising (i) an oil-in-water emulsion adjuvant (ii) a diphtheria toxoid, a tetanus toxoid, a pertussis toxoid, and a Hib conjugate (iii) a hepatitis B virus surface antigen and/or an inactivated poliovirus antigen. The composition is ideally aluminium-free.

The aluminium salt adjuvant advantageously has an adsorbed TLR agonist, as discussed below.

A further aspect of the invention is an immunisation schedule for an infant in which only one or two DTaP-containing compositions are administered. This aspect is explained in further detail below.

Diphtheria Toxoid

Diphtheria is caused by *Corynebacterium diphtheriae*, a Gram-positive non-sporing aerobic bacterium. This organism expresses a prophage-encoded ADP-ribosylating exotoxin ('diphtheria toxin'), which can be treated (e.g. using formaldehyde) to give a toxoid that is no longer toxic but that remains antigenic and is able to stimulate the production of specific anti-toxin antibodies after injection. Diphtheria toxoids are disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation.

The toxoided material may then be treated by a process comprising sterile filtration and/or dialysis.

Quantities of diphtheria toxoid can be expressed in international units (IU). For example, the NIBSC [6] supplies the 'Diphtheria Toxoid Adsorbed Third International Standard 1999' [7,8], which contains 160 IU per ampoule. As an alternative to the IU system, the 'Lf' unit ("flocculating units", the "limes flocculating dose", or the "limit of flocculation") is defined as the amount of toxoid which, when mixed with one International Unit of antitoxin, produces an optimally flocculating mixture [9]. For example, the NIBSC supplies 'Diphtheria Toxoid, Plain' [10], which contains 300 Lf per ampoule and 'The 1st International Reference Reagent For Diphtheria Toxoid For Flocculation Test' [11] which contains 900 Lf per ampoule. The concentration of diphtheria toxin in a composition can readily be determined using a flocculation assay by comparison with a reference material calibrated against such reference reagents. The conversion between IU and Lf systems depends on the particular toxoid preparation.

In some embodiments of the invention a composition includes a 'low dose' of diphtheria toxoid. This means that the concentration of diphtheria toxoid in the composition is ≤8 Lf/ml e.g. <7, <6, <5, <4 <3, <2, <1 Lf/ml, etc. In a typical 0.5 ml unit dose volume, therefore, the amount of diphtheria toxoid is less than 4 Lf e.g. <3, <2, <1, <½ Lf, etc.

Where a composition of the invention includes an aluminium salt adjuvant then diphtheria toxoid in the composition is preferably adsorbed (more preferably totally adsorbed) onto that salt, preferably onto an aluminium hydroxide adjuvant.

Tetanus Toxoid

Tetanus is caused by *Clostridium tetani*, a Gram-positive, spore-forming bacillus. This organism expresses an endopeptidase ('tetanus toxin'), which can be treated to give a toxoid that is no longer toxic but that remains antigenic and is able to stimulate the production of specific anti-toxin antibodies after injection. Tetanus toxoids are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

Quantities of tetanus toxoid can be expressed in international units (IU). For example, NIBSC supplies the 'Tetanus Toxoid Adsorbed Third International Standard 2000' [12, 13], which contains 469 IU per ampoule. As with diphtheria toxoid, the 'Lf' unit is an alternative to the IU system. NIBSC supplies 'The 1st International Reference Reagent for Tetanus Toxoid For Flocculation Test' [14] which contains 1000 LF per ampoule. The concentration of diphtheria toxin in a composition can readily be determined using a flocculation assay by comparison with a reference material calibrated against such reference reagents.

In some embodiments of the invention a composition includes a 'low dose' of tetanus toxoid. This means that the concentration of tetanus toxoid in the composition is ≤3.5 Lf/ml e.g. <3, <2.5, <2, <1.5 <1, <½ Lf/ml, etc. In a typical 0.5 ml unit dose volume, therefore, the amount of tetanus toxoid is less than 1.75 Lf e.g. <1.5, <1, <½, <¼ Lf, etc.

Where a composition of the invention includes an aluminium salt adjuvant then tetanus toxoid in the composition is preferably adsorbed (sometimes totally adsorbed) onto that salt, preferably onto an aluminium hydroxide adjuvant.

Pertussis Toxoid

*Bordetella pertussis* causes whooping cough. Pertussis antigens in vaccines are either cellular (whole cell, in the form of inactivated *B. pertussis* cells; 'wP') or acellular ('aP'). Preparation of cellular pertussis antigens is well documented (e.g. see chapter 21 of reference 1) e.g. it may be obtained by heat inactivation of phase I culture of *B. pertussis*. Where acellular antigens are used, one, two or (preferably) three of the following antigens are included: (1) detoxified pertussis toxin (pertussis toxoid, or 'PT'); (2) filamentous hemagglutinin ('FHA'); (3) pertactin (also known as the '69 kiloDalton outer membrane protein'). These three antigens can be prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography, or by IMAC. FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [15] (e.g. the 9K/129G double mutant [16]), but detoxification by chemical treatment is preferred.

The invention can use a PT-containing wP antigen or, preferably, a PT-containing aP antigen. When using an aP antigen a composition of the invention will typically, in addition to the PT, include FHA and, optionally, pertactin. It can also optionally include fimbriae types 2 and 3.

Quantities of acellular pertussis antigens are typically expressed in micrograms. In some embodiments of the invention a composition includes a 'low dose' of pertussis toxoid. This means that the concentration of pertussis toxoid in the composition is ≤5 μg/ml e.g. <4, <3, <2.5, <2, <1 μg/ml, etc. In a typical 0.5 ml unit dose volume, therefore, the amount of pertussis toxoid is less than 2.5 μg e.g. <2, <1.5, <1, <0.5 μg, etc.

Where a composition of the invention includes an aluminium salt adjuvant then pertussis toxoid in the composition is preferably adsorbed (sometimes totally adsorbed) onto that salt, preferably onto an aluminium hydroxide adjuvant. Any FHA can also be adsorbed to an aluminium hydroxide adjuvant. Any pertactin can be adsorbed to an aluminium phosphate adjuvant.

Hib Conjugates

*Haemophilus influenzae* type b ('Hib') causes bacterial meningitis. Hib vaccines are typically based on the capsular saccharide antigen (e.g. chapter 14 of ref. 1), the preparation of which is well documented (e.g. references 17 to 26). The Hib saccharide is conjugated to a carrier protein in order to enhance its immunogenicity, especially in children. Typical carrier proteins are tetanus toxoid, diphtheria toxoid, the CRM197 derivative of diphtheria toxoid, *H. influenzae* protein D, and an outer membrane protein complex from serogroup B meningococcus. Tetanus toxoid is a preferred carrier, as used in the product commonly referred to as 'PRP-T'. PRP-T can be made by activating a Hib capsular polysaccharide using cyanogen bromide, coupling the activated saccharide to an adipic acid linker (such as (1-ethyl-3-(3-dimethylaminopropyl) carbodiimide), typically the hydrochloride salt), and then reacting the linker-saccharide entity with a tetanus toxoid carrier protein. The saccharide moiety of the conjugate may comprise full-length polyribosylribitol phosphate (PRP) as prepared from Hib bacteria, and/or fragments of full-length PRP. Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred vaccines, however, the weight ratio of saccharide to carrier protein is between 1:2.5 and 1:3.5. In vaccines where tetanus toxoid is present both as an antigen and as a carrier protein then the weight ratio of saccharide to carrier protein in the conjugate may be between 1:0.3 and 1:2 [27]. Administration of the Hib conjugate preferably results in an anti-PRP antibody concentration of ≥0.15 µg/ml, and more preferably ≥1 µg/ml, and these are the standard response thresholds.

Quantities of Hib antigens are typically expressed in micrograms. For conjugate antigens this figure is based on the saccharide content of the conjugate. In some embodiments of the invention a composition includes a 'low dose' of a Hib conjugate. This means that the concentration of Hib saccharide in the composition is ≤5 µg/ml e.g. <4, <3, <2.5, <2, <1, etc. In a typical 0.5 ml unit dose volume, therefore, the amount of Hib is less than 2.5 µg e.g. <2, <1.5, <1, <0.5, etc.

Where a composition of the invention includes an aluminium salt adjuvant then Hib conjugate can be adsorbed onto that salt or can be unadsorbed.

Hepatitis B Virus Surface Antigen

Hepatitis B virus (HBV) is one of the known agents which causes viral hepatitis. The HBV virion consists of an inner core surrounded by an outer protein coat or capsid, and the viral core contains the viral DNA genome. The major component of the capsid is a protein known as HBV surface antigen or, more commonly, 'HBsAg', which is typically a 226-amino acid polypeptide with a molecular weight of ~24 kDa. All existing hepatitis B vaccines contain HBsAg, and when this antigen is administered to a normal vaccine it stimulates the production of anti-HBsAg antibodies which protect against HBV infection.

For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention is recombinantly expressed in yeast cells. Suitable yeasts include *Saccharomyces* (such as *S. cerevisiae*) or *Hanensula* (such as *H. polymorpha*) hosts.

Unlike native HBsAg (i.e. as in the plasma-purified product), yeast-expressed HBsAg is generally non-glycosylated, and this is the most preferred form of HBsAg for use with the invention. Yeast-expressed HBsAg is highly immunogenic and can be prepared without the risk of blood product contamination.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [28]. The particles may retain non-ionic surfactant (e.g. polysorbate 20) if this was used during disruption of yeast [29].

A preferred method for HBsAg purification involves, after cell disruption: ultrafiltration; size exclusion chromatography; anion exchange chromatography; ultracentrifugation; desalting; and sterile filtration. Lysates may be precipitated after cell disruption (e.g. using a polyethylene glycol), leaving HBsAg in solution, ready for ultrafiltration.

After purification HBsAg may be subjected to dialysis (e.g. with cysteine), which can be used to remove any mercurial preservatives such as thimerosal that may have been used during HBsAg preparation [30]. Thimerosal-free preparation is preferred.

The HBsAg is preferably from HBV subtype adw2.

Quantities of HBsAg are typically expressed in micrograms. In some embodiments of the invention a composition includes a 'low dose' of HBsAg. This means that the concentration of HBsAg in the composition is ≤5 µg/ml e.g. <4, <3, <2.5, <2, <1, etc. In a typical 0.5 ml unit dose volume, therefore, the amount of HBsAg is less than 2.5 µg e.g. <2, <1.5, <1, <0.5, etc.

Where a composition of the invention includes an aluminium salt adjuvant then HBsAg can be adsorbed onto that salt (preferably adsorbed onto an aluminium phosphate adjuvant).

Inactivated Poliovirus Antigen (IPV)

Poliomyelitis can be caused by one of three types of poliovirus. The three types are similar and cause identical symptoms, but they are antigenically very different and infection by one type does not protect against infection by others. As explained in chapter 24 of reference 1, it is therefore preferred to use three poliovirus antigens with the invention—poliovirus Type 1 (e.g. Mahoney strain), poliovirus Type 2 (e.g. MEF-1 strain), and poliovirus Type 3 (e.g. Saukett strain). As an alternative to these strains, Sabin strains of types 1 to 3 can be used e.g. as discussed in references 31 & 32.

Polioviruses may be grown in cell culture. A preferred culture uses a Vero cell line, which is a continuous cell line derived from monkey kidney. Vero cells can conveniently be cultured microcarriers. Culture of the Vero cells before and during viral infection may involve the use of bovine-derived material, such as calf serum, and of lactalbumin hydrolysate (e.g. obtained by enzymatic degradation of lactalbumin). Such bovine-derived material should be obtained from sources which are free from BSE or other TSEs.

After growth, virions may be purified using techniques such as ultrafiltration, diafiltration, and chromatography. Prior to administration to patients, polioviruses must be inactivated, and this can be achieved by treatment with formaldehyde before the viruses are used in the process of the invention.

The viruses are preferably grown, purified and inactivated individually, and are then combined to give a bulk mixture for use with the invention.

Quantities of inactivated poliovirus (IPV) are typically expressed in the 'DU' unit (the "D-antigen unit" [33]). In some embodiments of the invention a composition includes a 'low dose' of a poliovirus. For a Type 1 poliovirus this means that the concentration of the virus in the composition is ≤20 DU/ml e.g. <18, <16, <14, <12, <10, etc. For a Type 2 poliovirus this means that the concentration of the virus in the composition is ≤4 DU/ml e.g. <3, <2, <1, <0.5, etc. For a Type 3 poliovirus this means that the concentration of the virus in the composition is ≤16 DU/ml e.g. <14, <12, <10, <8, <6, etc. Where all three of Types 1, 2 and 3 poliovirus are present the three antigens can be present at a DU ratio of 5:1:4 respectively, or at any other suitable ratio e.g. a ratio of 15:32:45 when using Sabin strains [31]. A low dose of antigen from Sabin strains is particularly useful, with ≤10 DU type 1, ≤20 DU type 2, and ≤30 DU type 3 (per unit dose).

Where a composition of the invention includes an aluminium salt adjuvant then polioviruses are preferably not adsorbed to any adjuvant before they are formulated, but after formulation they may become adsorbed onto any aluminium adjuvant(s) in the composition.

Further Antigens

As well as including D, T, Pa, HBsAg, Hib and/or poliovirus antigens, immunogenic compositions of the invention may include antigens from further pathogens. For example, these antigens may be from *N. meningitidis* (one or more of serogroups A, B, C, W135 and/or Y) or *S. pneumoniae.*

Meningococcal Saccharides

Where a composition includes a *Neisseria meningitidis* capsular saccharide conjugate there may be one or more than one such conjugate. Including 2, 3, or 4 of serogroups A, C, W135 and Y is typical e.g. A+C, A+W135, A+Y, C+W135, C+Y, W135+Y, A+C+W135, A+C+Y, A+W135+Y, A+C+W135+Y, etc. Components including saccharides from all four of serogroups A, C, W135 and Y are useful, as in the MENACTRA™ and MENVEO™ products. Where conjugates from more than one serogroup are included then they may be present at substantially equal masses e.g. the mass of each serogroup's saccharide is within +10% of each other. A typical quantity per serogroup is between 1 μg and 20 μg e.g. between 2 and 10 μg per serogroup, or about 4 μg or about 5 μg or about 10 μg. As an alternative to a substantially equal ratio, a double mass of serogroup A saccharide may be used.

Administration of a conjugate preferably results in an increase in serum bactericidal assay (SBA) titre for the relevant serogroup of at least 4-fold, and preferably at least 8-fold. SBA titres can be measured using baby rabbit complement or human complement [34].

The capsular saccharide of serogroup A meningococcus is a homopolymer of (α1→6)-linked N-acetyl-D-mannosamine-1-phosphate, with partial 0-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are 0-acetylated at the C-3 position. Acetyl groups can be replaced with blocking groups to prevent hydrolysis [35], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8 OAc-(α2→. Most serogroup C strains have O-acetyl groups at C-7 and/or C-8 of the sialic acid residues, but about 15% of clinical isolates lack these O-acetyl groups [36,37]. The presence or absence of OAc groups generates unique epitopes, and the specificity of antibody binding to the saccharide may affect its bactericidal activity against O-acetylated (OAc−) and de-O-acetylated (OAc+) strains [38-40]. Serogroup C saccharides used with the invention may be prepared from either OAc+ or OAc− strains. Licensed MenC conjugate vaccines include both OAc− (NEISVAC-C™) and OAc+ (MENJUGATE™ & MENINGITEC™) saccharides. In some embodiments, strains for production of serogroup C conjugates are OAc+ strains, e.g. of serotype 16, serosubtype P1.7a,1, etc. Thus C:16:P1.7a,1 OAc+ strains may be used. OAc+ strains in serosubtype P1.1 are also useful, such as the C11 strain. Preferred MenC saccharides are taken from OAc+ strains, such as strain C11.

The serogroup W135 saccharide is a polymer of sialic acid-galactose disaccharide units. Like the serogroup C saccharide, it has variable O-acetylation, but at sialic acid 7 and 9 positions [41]. The structure is written as: →4)-D-Neup5Ac(7/9OAc)-α-(2→6)-D-Gal-α-(1→.

The serogroup Y saccharide is similar to the serogroup W135 saccharide, except that the disaccharide repeating unit includes glucose instead of galactose. Like serogroup W135, it has variable O-acetylation at sialic acid 7 and 9 positions [41]. The serogroup Y structure is written as: →4)-D-Neup5Ac(7/9OAc)-α-(2→6)-D-Glc-α-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides. For example, reference 42 reports the use of serogroup Y saccharides that are more than 80% de-O-acetylated.

The saccharide moieties in meningococcal conjugates may comprise full-length saccharides as prepared from meningococci, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. One depolymerisation method involves the use of hydrogen peroxide [43]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [44]. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. In some embodiments, saccharides have the following range of average degrees of polymerisation (Dp): A=10-20; C=12-22; W135=15-25; Y=15-25. In terms of molecular weight, rather than Dp, useful ranges are, for all serogroups: <100 kDa; 5 kDa-75 kDa; 7 kDa-50 kDa; 8 kDa-35 kDa; 12 kDa-25 kDa; 15 kDa-22 kDa. In other embodiments, the average molecular weight for saccharides from each of meningococcal serogroups A, C, W135 and Y may be more than 50 kDa e.g. ≥75 kDa, ≥100 kDa, ≥110 kDa, ≥120 kDa, ≥130 kDa, etc. [45], and even up to 1500 kDa, in particular as determined by MALLS. For instance: a MenA saccharide may be in the range 50-500 kDa e.g. 60-80 kDa; a MenC saccharide may be in the range 100-210 kDa; a MenW135 saccharide may be in the range 60-190 kDa e.g. 120-140 kDa; and/or a MenY saccharide may be in the range 60-190 kDa e.g. 150-160 kDa.

If a component or composition includes both Hib and meningococcal conjugates then, in some embodiments, the mass of Hib saccharide can be substantially the same as the mass of a particular meningococcal serogroup saccharide. In some embodiments, the mass of Hib saccharide will be more than (e.g. at least 1.5×) the mass of a particular meningococcal serogroup saccharide. In some embodiments, the mass of Hib saccharide will be less than (e.g. at least 1.5× less) the mass of a particular meningococcal serogroup saccharide.

Where a composition includes saccharide from more than one meningococcal serogroup, there is an mean saccharide mass per serogroup. If substantially equal masses of each serogroup are used then the mean mass will be the same as each individual mass; where non-equal masses are used then the mean will differ e.g. with a 10:5:5:5 μg amount for a MenACWY mixture, the mean mass is 6.25 μg per serogroup. In some embodiments, the mass of Hib saccharide will be substantially the same as the mean mass of meningococcal saccharide per serogroup. In some embodiments, the mass of Hib saccharide will be more than (e.g. at least 1.5×) the mean mass of meningococcal saccharide per serogroup. In some embodiments, the mass of Hib saccharide will be less than (e.g. at least 1.5×) the mean mass of meningococcal saccharide per serogroup [46].

Meningococcal Polypeptides

The capsular saccharide of *Neisseria meningitidis* serogroup B is not a useful vaccine immunogen and so polypeptide antigens can be used instead. For instance, the "universal vaccine for serogroup B meningococcus" reported by Novartis Vaccines in ref. 47 can be used with the invention.

A composition of the invention can include a factor H binding protein (fHBP) antigen. The fHBP antigen has been characterised in detail. It has also been known as protein '741' [SEQ IDs 2535 & 2536 in ref. 48], 'NMB1870', 'GNA1870' [refs. 49-51], 'P2086', 'LP2086' or 'ORF2086' [52-54]. It is naturally a lipoprotein and is expressed across all meningococcal serogroups. The fHBP antigen falls into three distinct variants [55] and it is preferred to include antigens for all variants.

A composition of the invention may include a Neisserial Heparin Binding Antigen (NHBA) [56]. This antigen was included in the published genome sequence for meningococcal serogroup B strain MC58 [57] as gene NMB2132.

A composition of the invention may include a NadA antigen. The NadA antigen was included in the published genome sequence for meningococcal serogroup B strain MC58 [57] as gene NMB1994.

A composition of the invention may include a NspA antigen. The NspA antigen was included in the published genome sequence for meningococcal serogroup B strain MC58 [57] as gene NMB0663.

A composition of the invention may include a NhhA antigen. The NhhA antigen was included in the published genome sequence for meningococcal serogroup B strain MC58 [57] as gene NMB0992.

A composition of the invention may include an App antigen. The App antigen was included in the published genome sequence for meningococcal serogroup B strain MC58 [57] as gene NMB1985.

A composition of the invention may include an Omp85 antigen. Omp85 was included in the published genome sequence for meningococcal serogroup B strain MC58 [57] as gene NMB0182.

A composition of the invention may include a meningococcal outer membrane vesicle.

Pneumococcal Saccharides

*Streptococcus pneumoniae* causes bacterial meningitis and existing vaccines are based on capsular saccharides. Thus compositions of the invention can include at least one pneumococcal capsular saccharide conjugated to a carrier protein.

The invention can include capsular saccharide from one or more different pneumococcal serotypes. Where a composition includes saccharide antigens from more than one serotype, these are preferably prepared separately, conjugated separately, and then combined. Methods for purifying pneumococcal capsular saccharides are known in the art (e.g. see reference 58) and vaccines based on purified saccharides from 23 different serotypes have been known for many years. Improvements to these methods have also been described e.g. for serotype 3 as described in reference 59, or for serotypes 1, 4, 5, 6A, 6B, 7F and 19A as described in reference 60.

Pneumococcal capsular saccharide(s) will typically be selected from the following serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. Thus, in total, a composition may include a capsular saccharide from 1, 2, 3, 4, 5, 6, 7, 8, 9, 10, 11, 12, 13, 14, 15, 16, 17, 18, 19, 20, 21, 22, 23 or more different serotypes. Compositions which include at least serotype 6B saccharide are useful.

A useful combination of serotypes is a 7-valent combination e.g. including capsular saccharide from each of serotypes 4, 6B, 9V, 14, 18C, 19F, and 23F. Another useful combination is a 9-valent combination e.g. including capsular saccharide from each of serotypes 1, 4, 5, 6B, 9V, 14, 18C, 19F and 23F. Another useful combination is a 10-valent combination e.g. including capsular saccharide from each of serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; or 22F and 15B. A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F; 6A and 19A, etc.

Thus a useful 13-valent combination includes capsular saccharide from serotypes 1, 3, 4, 5, 6A, 6B, 7F, 9V, 14, 18C, 19 (or 19A), 19F and 23F e.g. prepared as disclosed in references 61 to 64. One such combination includes serotype 6B saccharide at about 8 μg/ml and the other 12 saccharides at concentrations of about 4 μg/ml each. Another such combination includes serotype 6A and 6B saccharides at about 8 μg/ml each and the other 11 saccharides at about 4 μg/ml each.

Suitable carrier proteins for conjugates include bacterial toxins, such as diphtheria or tetanus toxins, or toxoids or mutants thereof. These are commonly used in conjugate vaccines. For example, the CRM197 diphtheria toxin mutant is useful [65]. Other suitable carrier proteins include synthetic peptides [66,67], heat shock proteins [68,69], pertussis proteins [70,71], cytokines [72], lymphokines [72], hormones [72], growth factors [72], artificial proteins comprising multiple human $CD4^+$ T cell epitopes from various pathogen-derived antigens [73] such as N19 [74], protein D from *H. influenzae* [75-77], pneumolysin [78] or its non-toxic derivatives [79], pneumococcal surface protein PspA [80], iron-uptake proteins [81], toxin A or B from *C. difficile* [82], recombinant *Pseudomonas aeruginosa* exoprotein A (rEPA) [83], etc.

Particularly useful carrier proteins for pneumococcal conjugate vaccines are CRM197, tetanus toxoid, diphtheria toxoid and *H. influenzae* protein D. CRM197 is used in PREVNAR™. A 13-valent mixture may use CRM197 as the carrier protein for each of the 13 conjugates, and CRM197 may be present at about 55-60 μg/ml.

Where a composition includes conjugates from more than one pneumococcal serotype, it is possible to use the same carrier protein for each separate conjugate, or to use different carrier proteins. In both cases, though, a mixture of different conjugates will usually be formed by preparing each serotype conjugate separately, and then mixing them to form a mixture of separate conjugates. Reference 84 describes potential advantages when using different carrier proteins in multivalent pneumococcal conjugate vaccines, but the PREVNAR™ product successfully uses the same carrier for each of seven different serotypes.

A carrier protein may be covalently conjugated to a pneumococcal saccharide directly or via a linker. Various linkers are known. For example, attachment may be via a carbonyl, which may be formed by reaction of a free hydroxyl group of a modified saccharide with CDI [85,86] followed by reaction with a protein to form a carbamate linkage. Carbodiimide condensation can be used [87]. An adipic acid linker can be used, which may be formed by coupling a free —$NH_2$ group (e.g. introduced to a saccharide by amination) with adipic acid (using, for example, diimide activation), and then coupling a protein to the resulting saccharide-adipic acid intermediate [88,89]. Other linkers include β-propionamido [90], nitrophenyl-ethylamine [91], haloacyl halides [92], glycosidic linkages [93], 6-aminocaproic acid [94], N-succinimidyl-3-(2-pyridyldithio)-propionate (SPDP) [95], adipic acid dihydrazide ADH [96], $C_4$ to $C_{12}$ moieties [97], etc.

Conjugation via reductive amination can be used. The saccharide may first be oxidised with periodate to introduce an aldehyde group, which can then form a direct covalent linkage to a carrier protein via reductive amination e.g. to the ε-amino group of a lysine. If the saccharide includes multiple aldehyde groups per molecule then this linkage technique can lead to a cross-linked product, where multiple aldehydes react with multiple carrier amines. This cross-linking conjugation technique is particularly useful for at least pneumococcal serotypes 4, 6B, 9V, 14, 18C, 19F and 23F.

A pneumococcal saccharide may comprise a full-length intact saccharide as prepared from pneumococcus, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. Depolymerisation can be used in order to provide an optimum chain length for immunogenicity and/or to reduce chain length for physical manageability of the saccharides. Where more than one pneumococcal serotype is used then it is possible to use intact saccharides for each serotype, fragments for each serotype, or to use intact saccharides for some serotypes and fragments for other serotypes.

Where a composition includes saccharide from any of serotypes 4, 6B, 9V, 14, 19F and 23F, these saccharides are preferably intact. In contrast, where a composition includes saccharide from serotype 18C, this saccharide is preferably depolymerised.

A serotype 3 saccharide may also be depolymerised, For instance, a serotype 3 saccharide can be subjected to acid hydrolysis for depolymerisation [61] e.g. using acetic acid. The resulting fragments may then be oxidised for activation (e.g. periodate oxidation, may be in the presence of bivalent cations e.g. with $MgCl_2$), conjugated to a carrier (e.g. CRM197) under reducing conditions (e.g. using sodium cyanoborohydride), and then (optionally) any unreacted aldehydes in the saccharide can be capped (e.g. using sodium borohydride) [61]. Conjugation may be performed on lyophilized material e.g. after co-lyophilizing activated saccharide and carrier.

A serotype 1 saccharide may be at least partially de-O-acetylated e.g. achieved by alkaline pH buffer treatment [62] such as by using a bicarbonate/carbonate buffer. Such (partially) de-O-acetylated saccharides can be oxidised for activation (e.g. periodate oxidation), conjugated to a carrier (e.g. CRM197) under reducing conditions (e.g. using sodium cyanoborohydride), and then (optionally) any unreacted aldehydes in the saccharide can be capped (e.g. using sodium borohydride) [62]. Conjugation may be performed on lyophilized material e.g. after co-lyophilizing activated saccharide and carrier.

A serotype 19A saccharide may be oxidised for activation (e.g. periodate oxidation), conjugated to a carrier (e.g. CRM197) in DMSO under reducing conditions, and then (optionally) any unreacted aldehydes in the saccharide can be capped (e.g. using sodium borohydride) [98]. Conjugation may be performed on lyophilized material e.g. after co-lyophilizing activated saccharide and carrier.

One or more pneumococcal capsular saccharide conjugates may be present in lyophilised form.

Pneumococcal conjugates can ideally elicit anticapsular antibodies that bind to the relevant saccharide e.g. elicit an anti-saccharide antibody level ≥0.20 µg/mL [99]. The antibodies may be evaluated by enzyme immunoassay (EIA) and/or measurement of opsonophagocytic activity (OPA). The EIA method has been extensively validated and there is a link between antibody concentration and vaccine efficacy.

Aluminium Salt Adjuvants

In some embodiments, compositions of the invention include an aluminium salt adjuvant, although other embodiments may be aluminium-free.

Aluminium salt adjuvants currently in use are typically referred to either as "aluminium hydroxide" or as "aluminium phosphate" adjuvants. These are names of convenience, however, as neither is a precise description of the actual chemical compound which is present (e.g. see chapter 9 of reference 100). The invention can use any of the "hydroxide" or "phosphate" salts that useful as adjuvants.

Aluminium salts which include hydroxide ions are the preferred insoluble metal salts for use with the present invention as these hydroxide ions can readily undergo ligand exchange for adsorption of antigen and/or TLR agonists. Thus preferred salts for adsorption of TLR agonists are aluminium hydroxide and/or aluminium hydroxyphosphate. These have surface hydroxyl moieties which can readily undergo ligand exchange with phosphorus-containing groups (e.g. phosphates, phosphonates) to provide stable adsorption. An aluminium hydroxide adjuvant is most preferred.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 100). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants e.g. with needle-like particles with diameters about 2 nm. The PZC of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants known as "aluminium phosphate" are typically aluminium hydroxyphosphates, often also containing a small amount of sulfate. They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 0.99. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of ref. 100).

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate. Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

In solution both aluminium phosphate and hydroxide adjuvants tend to form stable porous aggregates 1-10 μm in diameter [101].

A composition can include a mixture of both an aluminium hydroxide and an aluminium phosphate, and components may be adsorbed to one or both of these salts.

An aluminium phosphate solution used to prepare a composition of the invention may contain a buffer (e.g. a phosphate or a histidine or a Tris buffer), but this is not always necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

In some embodiments of the invention a composition includes less than 0.2 mg $Al^{+++}$ per unit dose. The amount of $Al^{+++}$ can be lower than this e.g. <150 μg, <100 μg, <75 μg, <50 μg, <25 μg, <10 μg, etc.

In some embodiments of the invention a composition has an $Al^{+++}$ concentration below 0.4 mg/ml. The concentration of $Al^{+++}$ can be lower than this e.g. <300 μg/ml, <250 μg/ml, <200 μg/ml, <150 μg/ml, <100 μg/ml, <75 μg/ml, <50 μg/ml, <20 μg/ml, etc.

Where compositions of the invention include an aluminium-based adjuvant, settling of components may occur during storage. The composition should therefore be shaken prior to administration to a patient. The shaken composition will be a turbid white suspension.

Toll-Like Receptor Agonists

Where a composition of the invention includes an aluminium salt adjuvant then it is possible to adsorb a TLR agonist to that aluminium salt, thereby improving the immunopotentiating effect of the adjuvant [102]. This can lead to a better immune response and/or permits a reduction in the amount of aluminium in the composition while maintaining an equivalent adjuvant effect.

A composition of the invention can therefore include an aluminium salt (preferably an aluminium hydroxide) to which a TLR agonist (preferably a TLR7 agonist, and more preferably an agonist of human TLR7) is adsorbed. The agonist and the salt can form a stable adjuvant complex which retains the salt's ability to adsorb antigens.

TLR agonists with adsorptive properties typically include a phosphorus-containing moiety which can undergo ligand exchange with surface groups on an aluminium salt e.g. with surface hydroxide groups. Thus a useful TLR agonist may include a phosphate, a phosphonate, a phosphinate, a phosphonite, a phosphinite, a phosphate, etc. Preferred TLR agonists include at least one phosphate or phosphonate group [102].

Useful adsorptive TLR2 and TLR7 agonists are disclosed in references 102 to 106. Specific adsorptive TLR7 agonists of interest include, but are not limited to, compounds 1A to 27A in Table A on pages 79-84 of reference 107. For instance, the TLR7 agonist can be one of:

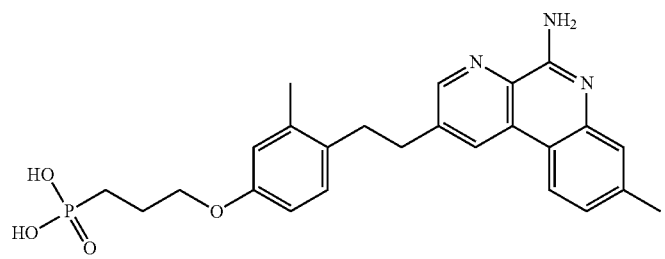

-continued
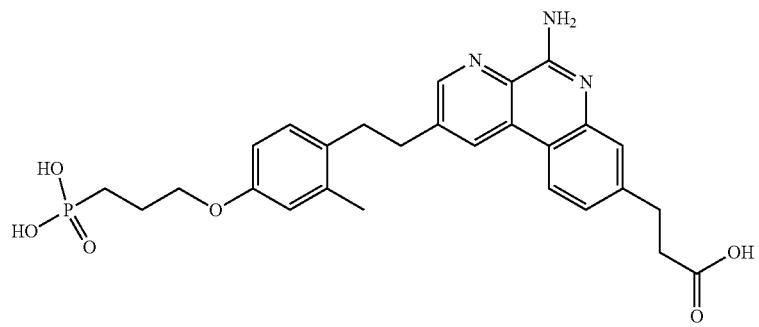
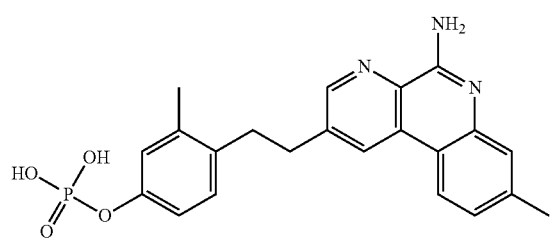
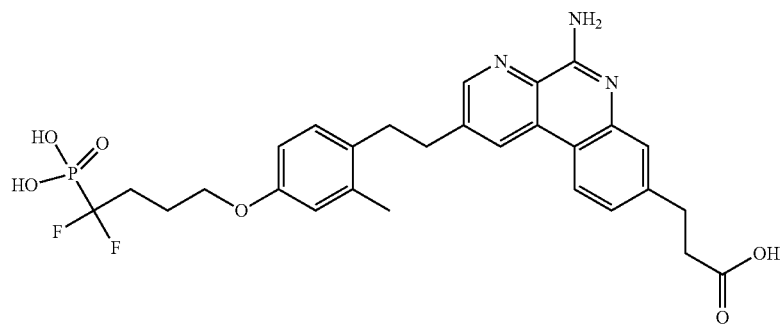
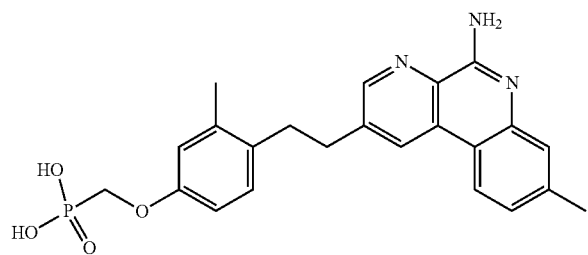
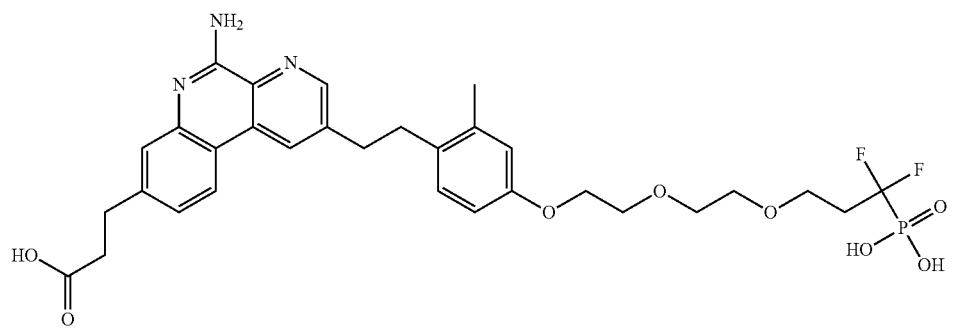
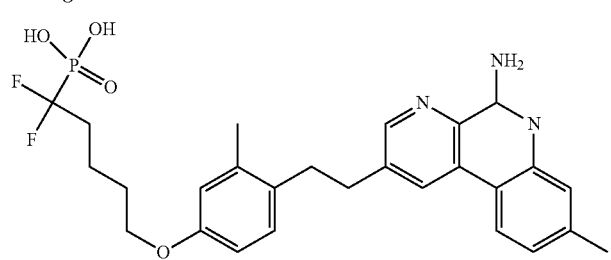

-continued
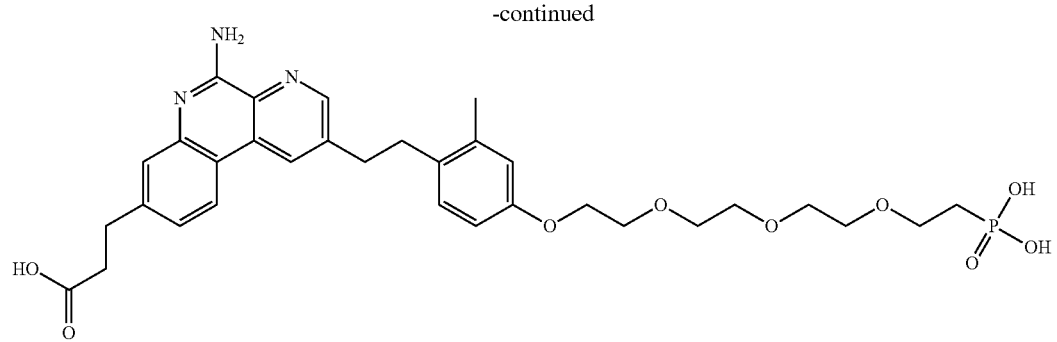
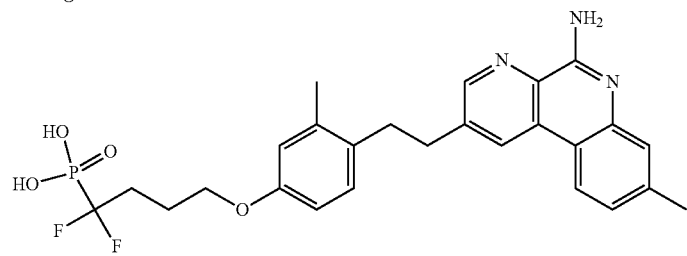
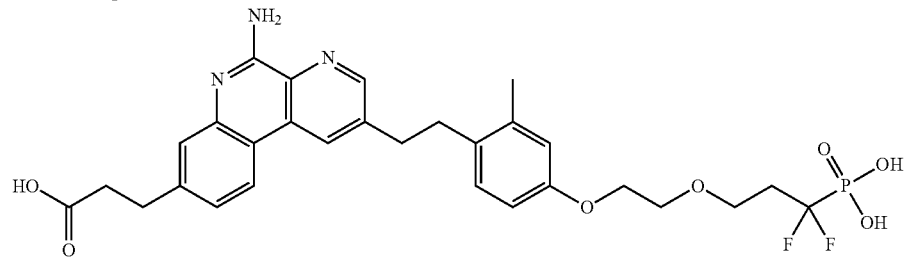
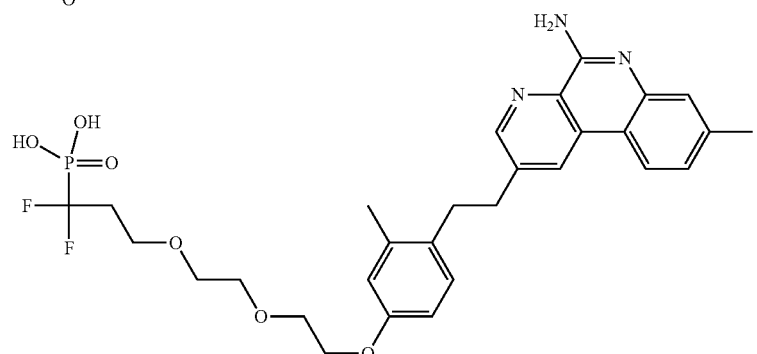
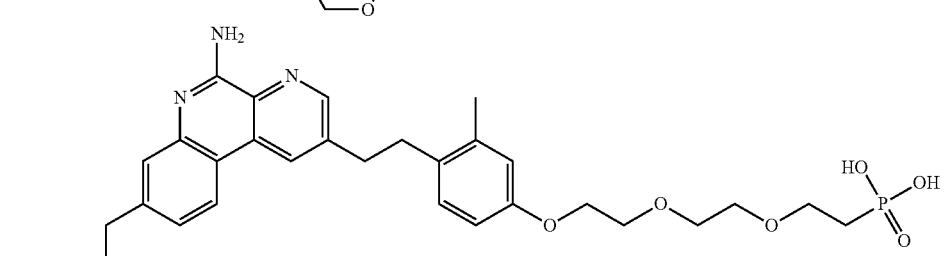
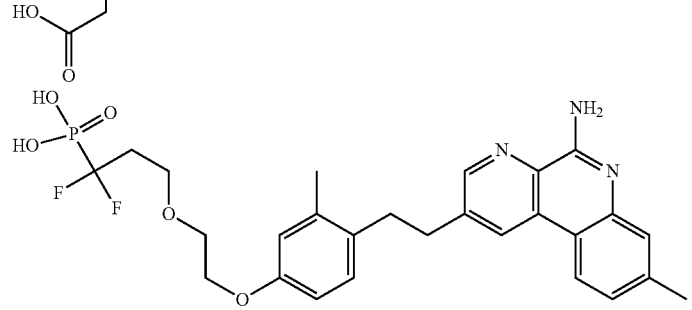

-continued
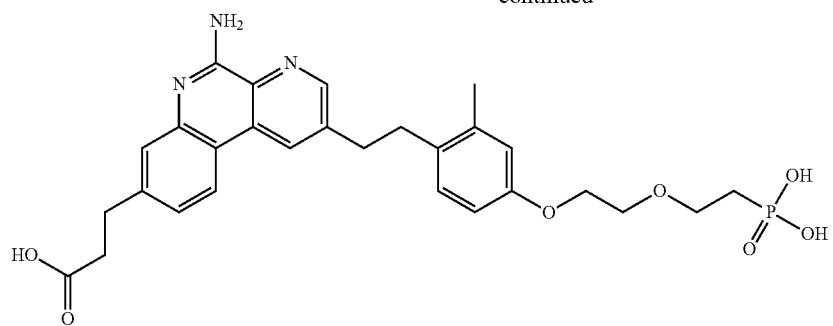
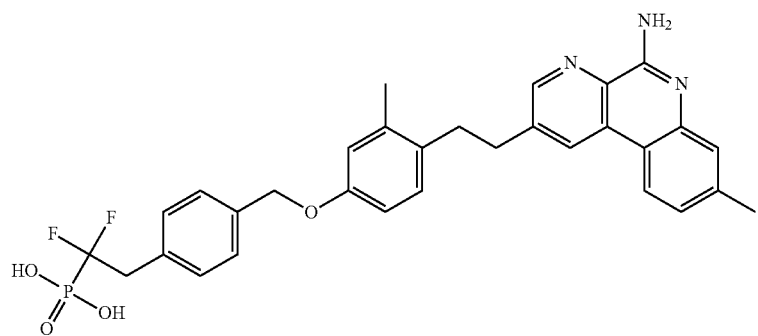
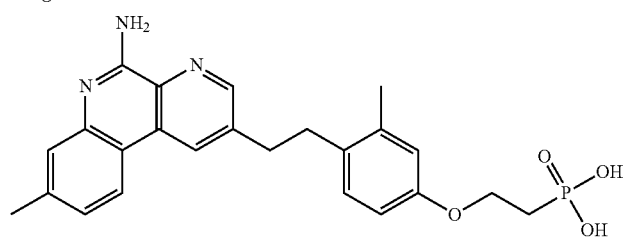
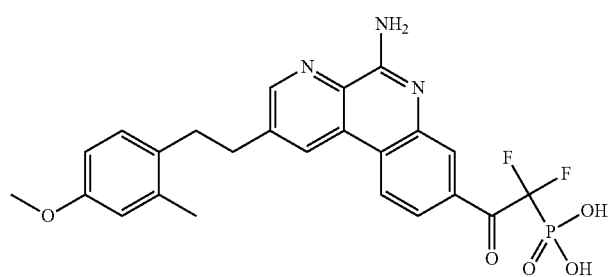
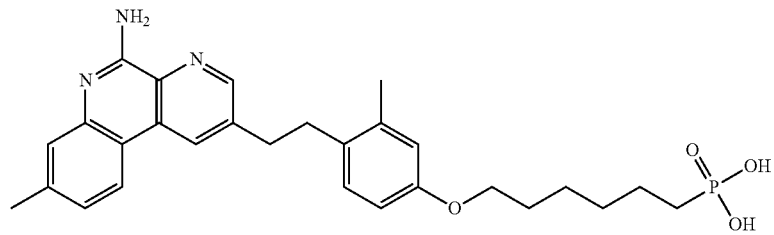
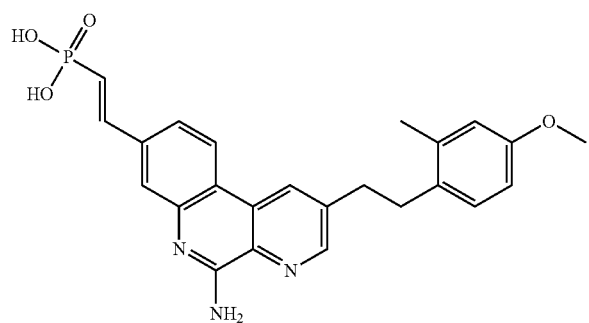

-continued
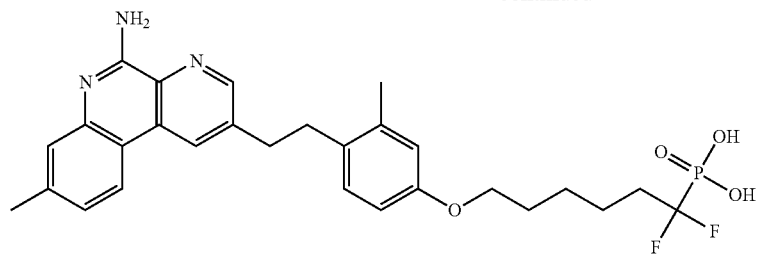
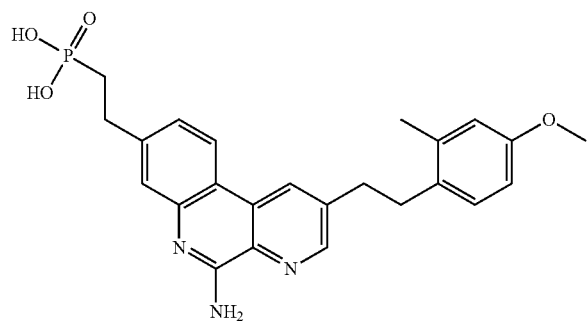
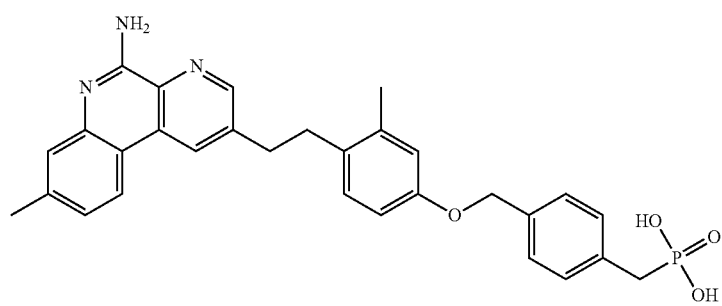
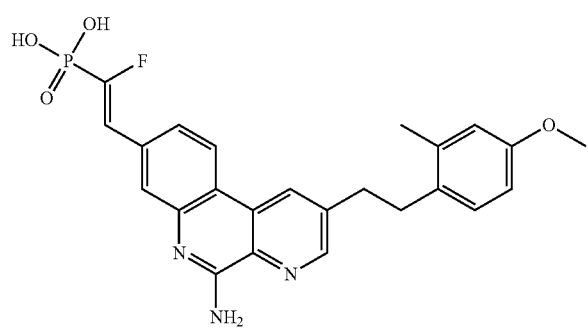
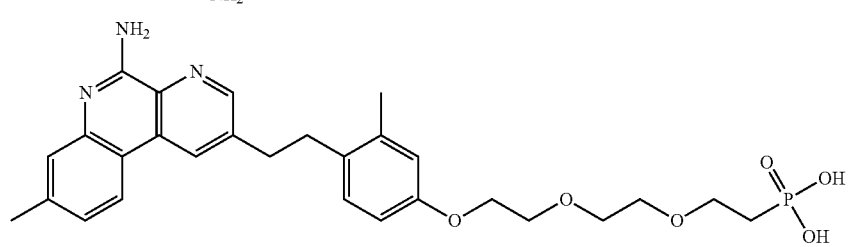
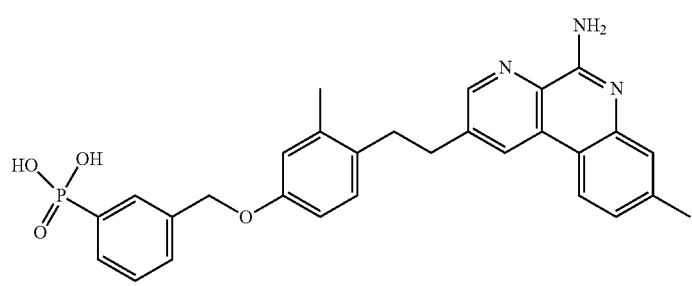

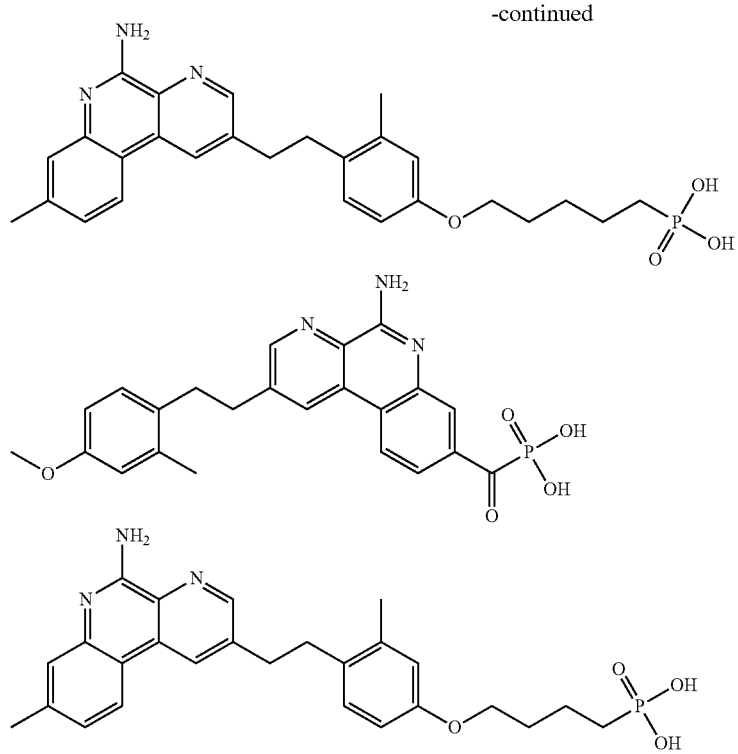

These compounds can be adsorbed to aluminium salt adjuvants by simple mixing. For instance, the compound (1 mg/mL) can be dissolved in 10 mM NaOH and added to a suspension of aluminium hydroxide adjuvant (2 mg/mL) to give a final TLR agonist concentration of 100 µg/dose. Preferably, 0.1 mg/mL, more preferably 0.01 mg/mL of the compound is added to 2 mg/mL aluminium hydroxide. The mass ratio of aluminium salt to TLR agonist is between 2:1 and 400:1, preferably 20:1, more preferably 200:1. Incubation at room temperature for 1 hour usually suffices for >90% adsorption. Adsorption can take place across a range of pH, e.g. from 6.5 to 9. In a preferred embodiment, an aluminium salt and a TLR agonist are prepared in histidine buffer e.g. between 5-20 mM (such as 10 mM) histidine buffer, conveniently at pH 6.5. For optimal antigen adsorption on aluminium hydroxide, the pH should be in the range between 6.0 and 6.5. The pH is also crucial for the integrity and stability of the antigens, and in case of protein antigens, for their proper folding in the final vaccine formulation.

One useful TLR7 agonist, which is used in the examples below, is 'compound T' (compound 6A on page 80 of reference 107). It has a solubility of about 4 mg/ml in water and adsorbs well to aluminium hydroxide:

In general, when a composition includes both a TLR agonist and an aluminium salt, the weight ratio of agonist to $Al^{+++}$ will be less than 5:1 e.g. less than 4:1, less than 3:1, less than 2:1, or less than 1:1. Thus, for example, with an $Al^{+++}$ concentration of 0.5 mg/ml the maximum concentration of TLR agonist would be 2.5 mg/ml. But higher or lower levels can be used. A lower mass of TLR agonist than of $Al^{+++}$ is typical e.g. per dose, 100 µg of TLR agonist with 0.2 mg $Al^{+++}$, etc.

The amount of TLR agonist in a unit dose will fall in a relatively broad range that can be determined through routine trials. An amount of between 1-1000 µg/dose can be used e.g. from 5-100 µg per dose or from 10-100 µg per dose, and ideally ≤300 µg per dose e.g. about 5 µg, 10 µg, 20 µg, 25 µg, 50 µg or 100 µg per dose. Thus the concentration of a TLR agonist in a composition of the invention may be from 2-2000 µg/ml e.g. from 10-200 µg/ml, or about 5, 10, 20, 40, 50, 100 or 200 µg/ml, and ideally ≤600 µg/ml.

It is preferred that at least 50% (by mass) of an agonist in the composition is adsorbed to the metal salt e.g. ≥60%, ≥70%, ≥80%, ≥85%, ≥90%, ≥92%, ≥94%, ≥95%, ≥96%, ≥97%, ≥98%, ≥99%, or even 100%.

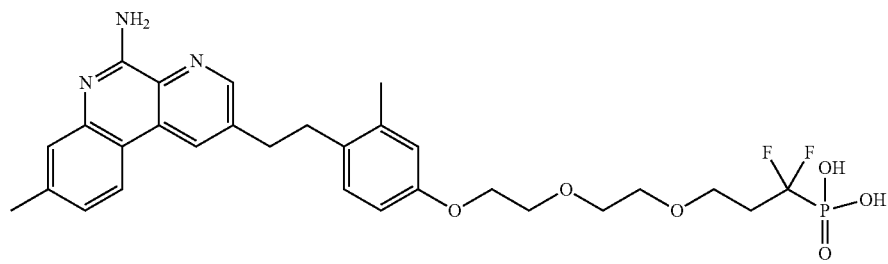 [SMILES: Cc1ccc2c(c1)nc(N)c1ncc(CCc3ccc(OCCOCCOCCC(F)(F)P(=O)(O)O)cc3C)cc12]

Where a composition of the invention includes a TLR agonist adsorbed to a metal salt, and also includes a buffer, it is preferred that the concentration of any phosphate ions in the buffer should be less than 50 mM (e.g. between 1-15 mM) as a high concentration of phosphate ions can cause desorption. Use of a histidine buffer is preferred.

Oil-In-Water Emulsion Adjuvants

Oil-in-water emulsions are known to be useful adjuvants e.g. MF59 and AS03 are both present in authorised vaccines in Europe. Various useful emulsion adjuvants are known, and they typically include at least one oil and at least one surfactant, with the oil(s) and surfactant(s) being biodegradable (metabolisable) and biocompatible. The oil droplets in the emulsion generally have a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are polysorbate 80 (polyoxyethylene sorbitan monooleate; Tween 80), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as polysorbate 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, polysorbate 80, and sorbitan trioleate. The composition of the emulsion by volume can be about 5% squalene, about 0.5% polysorbate 80 and about 0.5% sorbitan trioleate. In weight terms, these ratios become 4.3% squalene, 0.5% polysorbate 80 and 0.48% sorbitan trioleate. This adjuvant is known as 'MF59' [108-110], as described in more detail in Chapter 10 of ref. 100 and chapter 12 of ref. 111. The MF59 emulsion advantageously includes citrate ions e.g. 10 mM sodium citrate buffer.

An emulsion of squalene, a tocopherol, and polysorbate 80. The emulsion may include phosphate buffered saline. It may also include sorbitan trioleate (e.g. at 1%) and/or lecithin. These emulsions may have from 2 to 10% squalene, from 2 to 10% tocopherol and from 0.3 to 3% polysorbate 80, and the weight ratio of squalene:tocopherol is preferably ≤1 (e.g. 0.90) as this provides a more stable emulsion. Squalene and polysorbate 80 may be present volume ratio of about 5:2, or at a weight ratio of about 11:5. Thus the three components (squalene, tocopherol, polysorbate 80) may be present at a weight ratio of 1068:1186:485 or around 55:61:25. One such emulsion ('AS03') can be made by dissolving polysorbate 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [112] e.g. in the ratios discussed above.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 µg/ml polysorbate 80, 110 m/ml Triton X-100 and 100 µg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [113] (0.05-1% Thr-MDP, 5% squalane, 2.5% Pluronic L121 and 0.2% polysorbate 80). It can also be used without the Thr-MDP, as in the "AF" adjuvant [114] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [115]. The emulsion may also include one or more of: alditol; a cryoprotective agent (e.g. a sugar, such as dodecylmaltoside and/or sucrose); and/or an alkylpolyglycoside. It may also include a TLR4 agonist, such as one whose chemical structure does not include a sugar ring [116]. Such emulsions may be lyophilized.

An emulsion having from 0.5-50% of an oil, 0.1-10% of a phospholipid, and 0.05-5% of a non-ionic surfactant. As described in reference 117, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, polysorbate 80 or Span 80). Additives may be included, such as QuilA saponin, cholesterol, a saponin-lipophile conjugate (such as GPI-0100, described in reference 118, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.

An emulsion in which a saponin (e.g. QuilA or QS21) and a sterol (e.g. a cholesterol) are associated as helical micelles [119].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [120].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [120].

Preferred oil-in-water emulsions used with the invention comprise squalene and/or polysorbate 80.

The emulsions may be mixed with antigens during manufacture, or they may be mixed extemporaneously at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1. If emulsion and antigen are stored separately in a multidose kit (from which multiple unit doses can be taken) then the product may be presented as a vial containing emulsion and a vial containing aqueous antigen, for mixing to give adjuvanted liquid vaccine.

When used in formulating a vaccine, MF59 is preferably mixed with antigens in phosphate-buffered saline to preserve the long-term stability of MF59 formulations and to guarantee physiological pH and osmolarity values in the final vaccine. This mixing can be at a 1:1 volume ratio. The PBS can have pH 7.2.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group. They also have antioxidant properties that may help to stabilize the emulsions [121]. A preferred α-tocopherol is DL-α-tocopherol, and the preferred salt of this tocopherol is the succinate. The succinate salt has been found to cooperate with TNF-related ligands in vivo.

Immunogenic Compositions

Compositions of the invention may comprise: (a) an antigenic component; and (b) a non-antigenic component. The antigenic component can comprise or consist of the antigens discussed above. The non-antigenic component can include carriers, adjuvants, excipients, buffers, etc. These non-antigenic components may have various sources. For example, they may be present in one of the antigen or adjuvant materials that is used during manufacture or may be added separately from those components.

Preferred compositions of the invention include one or more pharmaceutical carrier(s) and/or excipient(s).

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 280-320 mOsm/kg. Osmolality has previously been reported not to have an impact on pain caused by vaccination [122], but keeping osmolality in this range is nevertheless preferred.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

A composition of the invention can be substantially free from surfactants (prior to mixing with any emulsion adjuvant). In particular, the composition of the invention can be substantially free from polysorbate 80 e.g. it contains less than 0.1 µg/ml of polysorbate 80, and preferably contains no detectable polysorbate 80. Where a composition includes HBsAg, however, it will usually include polysorbate 20 e.g. if it was used during yeast disruption [29].

The pH of a composition of the invention will generally be between 6.0 and 7.5. A manufacturing process may therefore include a step of adjusting the pH of a composition prior to packaging. Aqueous compositions administered to a patient can have a pH of between 5.0 and 7.5, and more typically between 5.0 and 6.0 for optimum stability; where a diphtheria toxoid and/or tetanus toxoid is present, the pH is ideally between 6.0 and 7.0.

Compositions of the invention are preferably sterile.

Compositions of the invention are preferably non-pyrogenic e.g. containing <1 EU (endotoxin unit, a standard measure; 1 EU is equal to 0.2 ng FDA reference standard Endotoxin EC-2 'RSE') per dose, and preferably <0.1 EU per dose.

Compositions of the invention are preferably gluten free.

Due to the adsorbed nature of antigens a vaccine product may be a suspension with a cloudy appearance. This appearance means that microbial contamination is not readily visible, and so the vaccine preferably contains an antimicrobial agent. This is particularly important when the vaccine is packaged in multidose containers. Preferred antimicrobials for inclusion are 2-phenoxyethanol and thimerosal. It is preferred, however, not to use mercurial preservatives (e.g. thimerosal) during the process of the invention. Thus, between 1 and all of the components used in the process may be substantially free from mercurial preservative. However, the presence of trace amounts may be unavoidable if a component was treated with such a preservative before being used in the invention. For safety, however, it is preferred that the final composition contains less than about 25 ng/ml mercury. More preferably, the final vaccine product contains no detectable thimerosal. This will generally be achieved by removing the mercurial preservative from an antigen preparation prior to its addition in the process of the invention or by avoiding the use of thimerosal during the preparation of the components used to make the composition. Mercury-free compositions are preferred.

Compositions of the invention will generally be in aqueous form.

During manufacture, dilution of components to give desired final concentrations will usually be performed with WFI (water for injection).

The invention can provide bulk material which is suitable for packaging into individual doses, which can then be distributed for administration to patients. Concentrations discussed above are typically concentrations in final packaged dose, and so concentrations in bulk vaccine may be higher (e.g. to be reduced to final concentrations by dilution).

Compositions of the invention are preferably administered to patients in 0.5 ml unit doses. References to 0.5 ml doses will be understood to include normal variance e.g. 0.5 ml±0.05 ml. For multidose situations, multiple dose amounts will be extracted and packaged together in a single container e.g. 5 ml for a 10-dose multidose container (or 5.5 ml with 10% overfill).

Residual material from individual antigenic components may also be present in trace amounts in the final vaccine produced by the process of the invention. For example, if formaldehyde is used to prepare the toxoids of diphtheria, tetanus and pertussis then the final vaccine product may retain trace amounts of formaldehyde (e.g. less than 10 µg/ml, preferably <5 µg/ml). Media or stabilizers may have been used during poliovirus preparation (e.g. Medium 199), and these may carry through to the final vaccine. Similarly, free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at ≤100 µg/ml, preferably <10 µg/ml, each. Other components from antigen preparations, such as neomycin (e.g. neomycin sulfate, particularly from a poliovirus component), polymyxin B (e.g. polymyxin B sulfate, particularly from a poliovirus component), etc. may also be present at sub-nanogram amounts per dose. A further possible component of the final vaccine which originates in the antigen preparations arises from less-than-total purification of antigens. Small amounts of *B. pertussis, C. diphtheriae, C. tetani* and *S. cerevisiae* proteins and/or genomic DNA may therefore be present. To minimize the amounts of these residual components, antigen preparations are preferably treated to remove them prior to the antigens being used with the invention.

Where a poliovirus component is used, it will generally have been grown on Vero cells. The final vaccine preferably contains less than 10 ng/ml, preferably ≤1 ng/ml e.g. ≤500 µg/ml or ≤50 µg/ml of Vero cell DNA e.g. less than 10 ng/ml of Vero cell DNA that is ≥50 base pairs long.

Compositions of the invention are presented for use in containers. Suitable containers include vials and disposable syringes (preferably sterile ones). Processes of the invention may comprise a step of packaging the vaccine into containers for use. Suitable containers include vials and disposable syringes (preferably sterile ones).

Where a composition of the invention is presented in a vial, this is preferably made of a glass or plastic material. The vial is preferably sterilized before the composition is added to it. To avoid problems with latex-sensitive patients, vials may be sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

After a composition is packaged into a container, the container can then be enclosed within a box for distribution e.g. inside a cardboard box, and the box will be labeled with details of the vaccine e.g. its trade name, a list of the antigens in the vaccine (e.g. 'hepatitis B recombinant', etc.), the presentation container (e.g. 'Disposable Prefilled Tip-Lok Syringes' or '10×0.5 ml Single-Dose Vials'), its dose (e.g. 'each containing one 0.5 ml dose'), warnings (e.g. 'For Adult Use Only' or 'For Pediatric Use Only'), an expiration date, an indication, a patent number, etc. Each box might contain more than one packaged vaccine e.g. five or ten packaged vaccines (particularly for vials).

The vaccine may be packaged together (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

The packaged vaccine is preferably stored at between 2° C. and 8° C. It should not be frozen.

Vaccines can be provided in full-liquid form (i.e. where all antigenic components are in aqueous solution or suspension) after manufacture, or they can be prepared in a form where the vaccine can be prepared extemporaneously at the time/point of use by mixing together two components. Such two-component embodiments include liquid/liquid mixing and liquid/solid mixing e.g. by mixing aqueous material with lyophilised material. For instance, in one embodiment a vaccine can be made by mixing: (a) a first component comprising aqueous antigens and/or adjuvant; and (b) a second component comprising lyophilized antigens. In another embodiment a vaccine can be made by mixing: (a) a first component comprising aqueous antigens and/or adjuvant; and (b) a second component comprising aqueous antigens. In another embodiment a vaccine can be made by mixing: (a) a first component comprising aqueous antigens; and (b) a second component comprising aqueous adjuvant. The two components are preferably in separate containers (e.g. vials and/or syringes), and the invention provides a kit comprising components (a) and (b).

Another useful liquid/lyophilised format comprises (a) an oil-in-water emulsion adjuvant and (b) a lyophilised component including one or more antigens. A vaccine composition suitable for patient administration is obtained by mixing components (a) and (b). In some embodiments component (a) is antigen-free, such that all antigenic components in the final vaccine are derived from component (b); in other embodiments component (a) includes one or more antigen(s), such that the antigenic components in the final vaccine are derived from both components (a) and (b).

Another useful liquid/lyophilised format comprises (a) an aqueous complex of an aluminium salt and a TLR agonist and (b) a lyophilised component including one or more antigens. A vaccine composition suitable for patient administration is obtained by mixing components (a) and (b). In some embodiments component (a) is antigen-free, such that all antigenic components in the final vaccine are derived from component (b); in other embodiments component (a) includes one or more antigen(s), such that the antigenic components in the final vaccine are derived from both components (a) and (b).

Thus the invention provides a kit for preparing a combination vaccine, comprising components (a) and (b) as noted above. The kit components are typically vials or syringes, and a single kit may contain both a vial and a syringe. The invention also provides a process for preparing such a kit, comprising the following steps: (i) preparing an aqueous component vaccine as described above; (ii) packaging said aqueous combination vaccine in a first container e.g. a syringe; (iii) preparing an antigen-containing component in lyophilised form; (iv) packaging said lyophilised antigen in a second container e.g. a vial; and (v) packaging the first container and second container together in a kit. The kit can then be distributed to physicians.

A liquid/lyophilised format is particularly useful for vaccines that include a conjugate component, particularly Hib and/or meningococcal and/or pneumococcal conjugates, as these may be more stable in lyophilized form. Thus conjugates may be lyophilised prior to their use with the invention.

Where a component is lyophilised it generally includes non-active components which were added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. A final vaccine obtained by aqueous reconstitution of the lyophilised material may thus contain lactose and/or sucrose. It is preferred to use amorphous excipients and/or amorphous buffers when preparing lyophilised vaccines [123].

Preferred compositions of the invention include (1) diphtheria, tetanus and pertussis toxoids, inactivated poliovirus for Types 1, 2 & 3, plus (2) hepatitis B virus surface antigen and/or a Hib conjugate. These compositions may consist of the antigens specified, or may further include antigens from additional pathogens (e.g. meningococcus). Thus the compositions can be used as vaccines themselves, or as components of further vaccines.

Where a composition includes both diphtheria and tetanus toxoids these may be present at various ratios. There is preferably an excess of diphtheria toxoid (measured in Lf units) e.g. between 2-4× more diphtheria toxoid than tetanus toxoid, such as 2.5× or 3× more.

Methods of Treatment, and Administration of the Vaccine

Compositions of the invention are suitable for administration to human patients, and the invention provides a method of raising an immune response in a patient, comprising the step of administering a composition of the invention to the patient.

The invention also provides a composition of the invention for use in medicine.

The invention also provides the use of (i) at least a diphtheria toxoid, a tetanus toxoid, and a pertussis toxoid and (ii) an aluminium salt adjuvant, in the manufacture of a combination vaccine which includes less than 0.2 mg $Al^{+++}$ per unit dose.

The invention also provides the use of (i) at least a diphtheria toxoid, a tetanus toxoid, and a pertussis toxoid and (ii) an aluminium salt adjuvant, in the manufacture of a combination vaccine which includes a low dose of each of a diphtheria toxoid, a tetanus toxoid, and a pertussis toxoid.

The invention also provides the use of (i) at least a diphtheria toxoid, a tetanus toxoid, and a pertussis toxoid and (ii) an aluminium salt adjuvant, in the manufacture of a combination vaccine which includes a low dose of each of a diphtheria toxoid, a tetanus toxoid, and a pertussis toxoid and has less than 0.2 mg Al$^{+++}$ per unit dose.

The invention also provides the use of (i) a diphtheria toxoid, a tetanus toxoid, a pertussis toxoid, and a Hib conjugate (ii) a hepatitis B virus surface antigen and/or an inactivated poliovirus antigen, and (iii) an oil-in-water emulsion adjuvant, in the manufacture of a combination vaccine.

Immunogenic compositions of the invention are preferably vaccines, for use in the prevention of at least diphtheria, tetanus, whooping cough. Depending on their antigen content the vaccines may also protect against bacterial meningitis, polio, hepatitis, etc.

In order to have full efficacy, a typical primary immunization schedule (particularly for a child) may involve administering more than one dose. For example, doses may be at: 0 & 6 months (time 0 being the first dose); at 0, 1, 2 & 6 months; at day 0, day 21 and then a third dose between 6 & 12 months; at 2, 4 & 6 months; at 3, 4 & 5 months; at 6, 10 & 14 weeks; at 2, 3 & 4 months; or at 0, 1, 2, 6 & 12 months.

Compositions can also be used as booster doses e.g. for children, in the second year of life.

Compositions of the invention can be administered by intramuscular injection e.g. into the arm or leg.

Infant Immunisation Schedule with Fewer Doses

As mentioned above, a further aspect of the invention is an immunisation schedule for an infant (i.e. a child between birth and 1 year of age) in which only one or two DTP-containing compositions are administered. Thus, in some embodiments, the invention delivers fewer doses compared to the current normal 3-dose schedule, but without loss of immunoprotective effect.

According to this aspect, therefore, the invention provides:

a method for immunising an infant against at least diphtheria, tetanus and pertussis (whooping cough), comprising administering to the infant no more than two doses of a combination vaccine comprising a diphtheria toxoid, a tetanus toxoid, and a pertussis toxoid.

a method for immunising an infant against at least diphtheria, tetanus and pertussis (whooping cough), comprising administering to the infant no more than two doses of a combination vaccine comprising a diphtheria toxoid, a tetanus toxoid, a pertussis toxoid, and an aluminium salt adjuvant, wherein each dose of the vaccine contains less than 0.2 mg Al$^{+++}$.

a method for immunising an infant against at least diphtheria, tetanus and pertussis (whooping cough), comprising administering to the infant no more than two doses of a combination vaccine comprising an aluminium salt adjuvant and a low dose of each of a diphtheria toxoid, a tetanus toxoid, and a pertussis toxoid.

a method for immunising an infant against at least diphtheria, tetanus and pertussis (whooping cough), comprising administering to the infant no more than two doses of a combination vaccine comprising (i) a low dose of each of a diphtheria toxoid, a tetanus toxoid, and a pertussis toxoid, and (ii) an aluminium salt adjuvant; wherein each dose of the vaccine contains less than 0.2 mg Al$^{+++}$.

a method for immunising an infant against at least diphtheria, tetanus and pertussis (whooping cough), comprising administering to the infant no more than two doses of a aluminium-free combination vaccine comprising a diphtheria toxoid, a tetanus toxoid, a pertussis toxoid, and an oil-in-water emulsion adjuvant. The vaccine may have a low dose of each of a diphtheria toxoid, a tetanus toxoid, and a pertussis toxoid.

use of at least a diphtheria toxoid, a tetanus toxoid, and a pertussis toxoid in the manufacture of a combination vaccine for immunising an infant against at least diphtheria, tetanus and pertussis, wherein the vaccine is prepared for administration to the infant by no more than two doses. The vaccine may: (i) include an aluminium salt adjuvant, in which case it may include less than 0.2 mg Al$^{+++}$ per unit dose; and/or (ii) have a low dose of each of a diphtheria toxoid, a tetanus toxoid, and a pertussis toxoid.

use of at least a diphtheria toxoid, a tetanus toxoid, and a pertussis toxoid in the manufacture of an aluminium-free combination vaccine for immunising an infant against at least diphtheria, tetanus and pertussis, wherein the vaccine is prepared for administration to the infant by no more than two doses. The vaccine may comprise, either during manufacture or at the point of use, an oil-in-water emulsion adjuvant. The vaccine may have a low dose of each of a diphtheria toxoid, a tetanus toxoid, and a pertussis toxoid.

a combination vaccine comprising at least a diphtheria toxoid, a tetanus toxoid, and a pertussis toxoid, for use in a method for immunising an infant against at least diphtheria, tetanus and pertussis (whooping cough) by administering to the infant no more than two doses of the combination vaccine. The vaccine may: (i) include an aluminium salt adjuvant, in which case it may include less than 0.2 mg Al$^{+++}$ per unit dose; and/or (ii) have a low dose of each of a diphtheria toxoid, a tetanus toxoid, and a pertussis toxoid.

an aluminium-free combination vaccine comprising at least an oil-in-water emulsion adjuvant, a diphtheria toxoid, a tetanus toxoid, and a pertussis toxoid, for use in a method for immunising an infant against at least diphtheria, tetanus and pertussis (whooping cough) by administering to the infant no more than two doses of the combination vaccine. The vaccine may have a low dose of each of a diphtheria toxoid, a tetanus toxoid, and a pertussis toxoid.

According to this aspect, where the vaccine includes an aluminium salt adjuvant then, as disclosed above, the vaccine can also include a TLR agonist which may be adsorbed to that aluminium salt.

According to this aspect, the combination vaccine includes a pertussis toxoid. This may be incorporated into the vaccine as a protein within a cellular pertussis antigen, but it is preferred to use an acellular pertussis antigen, as discussed in more detail above.

According to this aspect, no more than two doses of the vaccine are given to the infant i.e. the infant receives a single dose or two doses of the vaccine, but does not receive three (or more) doses. The infant may, though, receive a third (and maybe further) dose later in their life i.e. after their first birthday or after their second birthday.

The one or two dose(s) is/are preferably given to the infant (i) between 1 and 5 months of age (ii) between 2 and 4 months of age (iii) between 3 and 5 months of age (iv) between 6 and 16 weeks of age or (v) between 0 and 3 months of age. For instance, two doses may be given at (i) 1 & 2 months of age (ii) 2 & 4 months of age (iii) 3 & 4 months of age (iv) 2 & 3 months of age (v) 0 and 1 months of age, etc.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg can be used.

Amounts of conjugates are generally given in terms of mass of saccharide (i.e. the dose of the conjugate (carrier+saccharide) as a whole is higher than the stated dose) in order to avoid variation due to choice of carrier.

Where a composition includes an aluminium salt adjuvant then preferably it does not also include an oil-in-water emulsion adjuvant. Conversely, where a composition includes an oil-in-water emulsion adjuvant then preferably it does not also include an aluminium salt adjuvant.

Phosphorous-containing groups employed with the invention may exist in a number of protonated and deprotonated forms depending on the pH of the surrounding environment, for example the pH of the solvent in which they are dissolved. Therefore, although a particular form may be illustrated herein, it is intended, unless otherwise mentioned, for these illustrations to merely be representative and not limiting to a specific protonated or deprotonated form. For example, in the case of a phosphate group, this has been illustrated as —OP(O)(OH)$_2$ but the definition includes the protonated forms —[OP(O)(OH$_2$)(OH)]$^+$ and —[OP(O)(OH$_2$)$_2$]$^{2+}$ that may exist in acidic conditions and the deprotonated forms —[OP(O)(OH)(O)]$^-$ and [OP(O)(O)$_2$]$^{2-}$ that may exist in basic conditions. The invention encompasses all such forms.

TLR agonists can exist as pharmaceutically acceptable salts. Thus, the compounds may be used in the form of their pharmaceutically acceptable salts i.e. physiologically or toxicologically tolerable salt (which includes, when appropriate, pharmaceutically acceptable base addition salts and pharmaceutically acceptable acid addition salts).

In the case of TLR agonists shown herein which may exist in tautomeric forms (i.e. in keto or enol forms), the compound can be used in all such tautomeric forms.

Where a compound is administered to the body as part of a composition then that compound may alternatively be replaced by a suitable prodrug.

Where animal (and particularly bovine) materials are used in the culture of cells, they should be obtained from sources that are free from transmissible spongiform encephalopathies (TSEs), and in particular free from bovine spongiform encephalopathy (BSE).

BRIEF DESCRIPTION OF THE DRAWINGS

There are no drawings.

MODES FOR CARRYING OUT THE INVENTION

Adjuvant Adsorption to Antigens 3-valent (DTaP) or 6-valent (DTaP-HBsAg-IPV-Hib) vaccines were adjuvanted with aluminium hydroxide alone, aluminium hydroxide with pre-adsorbed 'compound T', poly(lactide-co-glycolide) microparticles ('PLG'), and MF59 oil-in-water emulsion. Aluminium hydroxide and aluminium hydroxide with pre-adsorbed 'compound T' were prepared in histidine buffer pH 6.5. At pH 6.5, aluminium hydroxide has a positive net charge, while most proteins have a negative net charge. The pH value was chosen to provide good adsorption of most of the tested antigens. All formulations adjuvanted with aluminium hydroxide or aluminium hydroxide with pre-adsorbed 'compound T' showed optimal pH (6.5-6.8±0.1) and osmolarity values (0.300±50 mO). Osmolarity was adjusted with NaCl. Antigens for the MF59-adjuvanted formulations were prepared in PBS. The resulting preparations had pH values between 6.2 and 7.3 and osmolarity values around 0.300±50 mO. Formulations containing PLG microparticles were prepared in water. PLG formulations showed suboptimal osmolarity values. The pH of the PLG formulations ranged from 5.8 to 6.5±0.1. The PLG microparticles were prepared with dioctylsulfosuccinate (DSS) which confers a negative net charge to the microparticles. Thus interaction of the microparticles with the antigen is mediated by positive charges on the antigen surface.

For aluminium hydroxide alone, aluminium hydroxide with pre-adsorbed 'compound T', and PLG, adsorption was detected by separating the adjuvant-antigen complexes from unadsorbed antigens by centrifugation. 0.4% DOC was added to the supernatant containing the unadsorbed antigens. Antigens were precipitated by the addition of 60% TCA and collected by centrifugation. The pellet containing the TCA-precipitated antigens was resuspended in loading buffer and loaded onto an SDS-PAGE gel. The pellet containing the adjuvant-antigen complexes was resuspended in desorption buffer (4× concentration: 0.5 M Na$_2$HPO$_4$ pH, 8 g SDS, 25 g glycerol, 6.16 g DTT and bromophenol blue), the aluminium hydroxide was removed by centrifugation and the supernatant applied to an SDS-PAGE gel. The MF59 oil-in-water emulsion containing antigens were separated by centrifugation in an oily phase and an aqueous phase. Both the aqueous phase containing unabsorbed antigens and the oily phase presumably containing MF59-associated antigens were mixed with loading buffer and applied to an SDS-PAGE gel. After electrophoretic separation of the samples, the gels were either analysed by Coomassie Blue staining or by Western blotting.

Using aluminium hydroxide alone at a concentration of 2 mg/ml, the adsorption profiles for DT, TT, PT, FHA and 69K detected by Coomassie Blue staining were complete both for the 3-valent formulation and the 6-valent formulation. No bands were detected in the DOC-TCA-treated supernatants. Western Blot analysis confirmed complete aluminium hydroxide adsorption for DT, TT, PT, FHA and 69K for both the 3-valent formulation and the 6-valent formulation. Likewise, the other five antigens—IPV1, IPV2, IPV3, HBsAg and Hib-CRM—did not show any detectable bands in the DOC-TCA-treated supernatants of aluminium hydroxide-adsorbed formulations. Thus all ten antigens present in the 6-valent formulation completely adsorbed to aluminium hydroxide.

For aluminium hydroxide with pre-adsorbed 'compound T', antigen adsorption differed between the 3-valent formulation and the 6-valent formulation. Four different 'compound T' concentrations were tested (0.1, 0.025, 0.01, 0.005 mg/ml). The aluminium hydroxide concentration was kept constant at 2 mg/ml. At 0.1 mg/ml 'compound T', all antigens in the 3-valent formulation were completely adsorbed. In contrast, 69K and PT in the 6-valent formulation were not completely adsorbed as determined by Coomassie Blue staining. At 0.01 mg/ml 'compound T', Western blot analysis confirmed adsorption of all ten antigens in the 6-valent formulation. Only a small amount of TT was still detectable in the supernatant using Western blot. The fact that TT could be detected in the supernatant by Western blot but not by SDS-PAGE is likely due to the greater sensitivity of the former method. Thus, at higher concentrations, 'compound T' appears to compete with the antigens for binding to the adjuvant. This could explain why the effect only becomes apparent in the presence of a greater number of antigens, i.e., when less aluminium hydroxide per antigen is available.

Using PLG microparticles, DT, TT, IPV1, IPV2, IPV3, FHA and CRM of the Hib-CRM conjugate were mostly presented on the supernatants with only very small amounts of DT, IPV1, IPV2 and FHA being detected by Western blot in the pellet containing the antigen-adjuvant complexes. 69K and PT seemed to be presented in similar amounts in supernatant and pellet. HBsAg could neither be detected in the supernatant nor in the pellet of the PLG formulations. In comparison to preparations containing aluminium hydroxide or aluminium hydroxide with pre-adsorbed 'compound T', PLG absorbed significantly less antigen. Moreover, the antigen adsorption profiles obtained using PLG showed an opposite trend to those seen in the presence of the other two adjuvants probably reflecting the negative net charge of PLG versus the positive net charge of aluminium hydroxide or aluminium hydroxide with pre-adsorbed 'compound T'.

MF59 is a delivery system generally considered unable to physically interact with the antigens as shown by the lack of an antigen deposition at the injection site and independent clearance of MF59 and the antigens (see references 124 and 125). 1:1, 1:3 and 1:10 ratios (v:v of MF59 to complete antigen formulation) were tested. For all three tested ratios, SDS-PAGE and Western blot analysis showed that all ten tested antigens were present in the aqueous phase of MF59-adjuvanted formulations. Thus the antigen profiles of MF59-adjuvanted formulations corresponded to the profiles of unadjuvanted formulations. The results confirmed that MF59 does not interact with any of the tested antigens.

Replacement or Reduction of Aluminium Salt Adjuvants

The INFANRIX HEXA product from GlaxoSmithKline contains ≥30 IU diphtheria toxoid, ≥40 IU tetanus toxoid, an acellular pertussis component (25/25/8 µg of PT/FHA/pertactin), 10 µg HBsAg, a trivalent IPV component (40/8/32 DU of types 1/2/3), and 10 µg Hib conjugate. The vaccine is presented as a 5-valent aqueous vaccine which is used to reconstitute the Hib conjugate from its lyophilised form, to give a 0.5 ml aqueous unit dose for human infants which contains 0.95 mg aluminium hydroxide and 1.45 mg aluminium phosphate.

To investigate alternative adjuvants (see above) a 6-valent mixture was adjuvanted with aluminium hydroxide alone (2 mg/ml in histidine buffer), with aluminium hydroxide with pre-adsorbed 'compound T' (see above; 1 mg/ml), with poly(lactide-co-glycolide) microparticles ('PLG', used at 40 mg/ml), or with the MF59 oil-in-water emulsion (mixed at equal volume with antigens in phosphate-buffered saline). The same diluents were used in all mouse experiments described below. Osmolarity of the formulations was adjusted with NaCl where necessary. An adjuvant-free control was also prepared. Antigen concentrations were as follows (per ml):

| DT | TT | PT | FHA | Pertactin |
| --- | --- | --- | --- | --- |
| 36.9 Lf | 14.8 Lf | 36.9 µg | 36.9 µg | 11.8 µg |
| IPV Type 1 | IPV Type 2 | IPV Type 3 | HBsAg | Hib |
| 59.1 DU | 11.8 DU | 47.3 DU | 14.8 µg | 14.8 µg |

The same adjuvants were also used with a 3-valent D-T-Pa mixture (same concentrations).

Osmolarity and pH were measured (and, if necessary, adjusted) after combining the components in order to ensure physiological acceptability. For all 3-valent compositions the pH was between 5.9 and 7.1 and osmolarity was between 290-320 mOsm/kg (except one at >400 mOsm/kg). For all 6-valent compositions the pH was between 5.5 and 6.8 and osmolarity was between 260-320 mOsm/kg (except one at >500 mOsm/kg). A buffer control had pH 7.3 and 276 mOsm/kg.

The integrity and immunogenicity of the combined antigens were also tested. None of antigens showed an altered analytical profile after being formulated as combinations i.e. the antigens and adjuvants are physically compatible together.

With aluminium hydroxide alone all antigens adsorbed well to the adjuvant. With aluminium hydroxide and compound 'T' (i.e. aluminium hydroxide which had been pre-mixed with 'compound T' to permit adsorption for formation of a stable adjuvant complex; 'Al-T' hereafter) all antigens adsorbed well, except that TT, pertactin and PT were partially desorbed.

With the PLG adjuvant the diphtheria and tetanus toxoids were unadsorbed but pertussis toxoid was adsorbed.

Mice (female Balb/c, 4 weeks old) were immunised intramuscularly with 100 µl of each composition (i.e. ⅕ human dose volume) at days 0 and 28. Sera were collected 14 days after each injection. After the second immunisation IgG antibody titers were as follows:

|  | No adjuvant | Al hydroxide | MF59 | PLG | Al-T | Infanrix-6 |
| --- | --- | --- | --- | --- | --- | --- |
| | | 3-valent vaccines | | | | |
| DT | 750 | 21626 | 15693 | 9430 | 23395 | — |
| TT | 13120 | 17868 | 22458 | 15917 | 23131 | — |
| Pertactin | 639 | 7209 | 10258 | 3946 | 12857 | — |
| PT | 2501 | 8270 | 7212 | 3679 | 9938 | — |
| FHA | 3982 | 12057 | 14098 | 14139 | 23008 | — |
| | | 6-valent vaccine | | | | |
| DT | 1751 | 18914 | 13982 | 7658 | 23102 | 21581 |
| TT | 12729 | 16756 | 22229 | 13744 | 23267 | 15998 |
| Pertactin | 333 | 6299 | 9363 | 2912 | 5153 | 10809 |
| PT | 3069 | 3384 | 4823 | 3906 | 6484 | 6052 |
| FHA | 4558 | 7206 | 16201 | 15206 | 19383 | 11051 |
| Hib | 177 | 813 | 1266 | 654 | 2153 | 1269 |
| HBsAg | 1058 | 1598 | 2288 | 1053 | 4501 | 1113 |

Thus for all of these antigens the inclusion of an adjuvant increased IgG antibody titers. The best titers were seen when using Al-T. The next best were with MF59, which gave better results than aluminium hydroxide alone. The titers obtained using Al-T were better for all antigens than those seen with Infanrix Hexa, except for pertactin.

Furthermore, the data show that the good results achieved with the 3-valent vaccine are maintained even after IPV, Hib and HBsAg are added.

IgG responses were also investigated by subclass. For most of the antigens in the 6-valent vaccines the adjuvants had little effect on IgG1 titers, but they did increase IgG2a and IgG2b titers. The best IgG2a and IgG2b titers were obtained with Al-T, and then with MF59.

The increased titers seen with Al-T compared with aluminium hydroxide alone, or with the mixture of aluminium salts seen in Infanrix Hexa, mean that the total amount of aluminium per dose can be reduced while maintaining enhancement of immune responses.

Reduction of Antigen Doses

Experiments were designed to investigate whether the improved adjuvants could be used to reduce the amount of antigen per dose. 10-fold, 50-fold and 100-fold dilutions (relative to human dosing i.e. to deliver 1 μg, 0.2 μg or 0.1 μg HBsAg to each mouse per 100 μl dose) of the 6-valent antigen combinations were made while adjuvant concentration was maintained.

Osmolarity and pH were measured (and, if necessary, adjusted) after dilution. For all 6-valent compositions the pH was between 6.1 and 7.0 and osmolarity was between 275-320 mOsm/kg. A buffer control had pH 7.3 and 285 mOsm/kg.

Mice were immunised in the same way as discussed above. Total serum IgG titers after 2 immunisations were as follows:

|  | No adjuvant | | | Al hydroxide | | | MF59 | | | Al-T | | |
| --- | --- | --- | --- | --- | --- | --- | --- | --- | --- | --- | --- | --- |
|  | 1/10 | 1/50 | 1/100 | 1/10 | 1/50 | 1/100 | 1/10 | 1/50 | 1/100 | 1/10 | 1/50 | 1/100 |
| DT | 459 | 2043 | 137 | 18357 | 13106 | 7541 | 17431 | 6003 | 8736 | 21913 | 16807 | 13724 |
| TT | 7602 | 7929 | 1700 | 17595 | 9664 | 5531 | 22791 | 12062 | 13015 | 23570 | 12237 | 13183 |
| Pertactin | 827 | 2154 | 341 | 10880 | 8135 | 4181 | 17159 | 10591 | 7288 | 17098 | 10748 | 8952 |
| PT | 3612 | 5645 | 2129 | 5287 | 3266 | 1068 | 7200 | 3659 | 5493 | 9051 | 4203 | 2717 |
| FHA | 2305 | 4161 | 101 | 8997 | 4471 | 1442 | 19197 | 5179 | 4492 | 22151 | 8293 | 3252 |
| Hib | 171 | 352 | 109 | 1380 | 796 | 251 | 3147 | 573 | 2415 | 3056 | 1440 | 1815 |
| HBsAg | 525 | 412 | 129 | 1034 | 685 | 226 | 4885 | 1103 | 1983 | 5270 | 1526 | 950 |

Thus the presence of adjuvants allowed a dose reduction of 5-fold or 10-fold while maintaining IgG titers which are comparable or higher to unadjuvanted antigens. MF59 and Al—T in particular are useful for dose sparing of antigens in this manner.

Adjuvant Dosing

With the 100-fold antigen dilution the amount of adjuvant was also reduced. The MF59 emulsion was mixed with antigens at a 1:1 volume ratio or at a 1:3 ratio (i.e. 1 ml of emulsion for every 3 ml of antigen, with 2 ml of buffer to maintain total volume) or at a 1:10 ratio. The Al-T complex was prepared at 3 strengths having 2 mg/ml aluminium hydroxide with either 5 μg, 25 μg or 100 μg of 'compound T' per dose. For comparison a 1:100 antigen dose was tested in unadjuvanted form or with aluminium hydroxide alone. A 1:100 dilution of Infanrix Hexa was also used for comparison. Osmolarity and pH were measured (and, if necessary, adjusted) after mixing (except for Infanrix Hexa). For all 6-valent compositions the pH was between 6.2 and 7.3 and osmolarity was between 270-320 mOsm/kg. A buffer control had pH 7.3 and 280 mOsm/kg.

Mice were immunised as before. Total serum IgG titers after 2 immunisations were as follows:

|  | No adjuvant | Infanrx Hexa | Al hydroxide | MF59 (v:v) | | | Al-T (μg 'T') | | |
| --- | --- | --- | --- | --- | --- | --- | --- | --- | --- |
|  |  |  |  | 1:1 | 1:3 | 1:10 | 100 | 25 | 5 |
| DT | 584 | 6282 | 10849 | 7786 | 4094 | 8442 | 21571 | 20865 | 11788 |
| TT | 3426 | 5415 | 6857 | 11506 | 9197 | 11422 | 16041 | 15124 | 6236 |
| Pertactin | 48 | 3017 | 6053 | 8838 | 2970 | 2876 | 6158 | 6697 | 3815 |
| PT | 3351 | 1751 | 2699 | 4406 | 5072 | 6020 | 2476 | 2696 | 3079 |
| FHA | 262 | 7886 | 5626 | 14700 | 11340 | 10205 | 7369 | 8634 | 6120 |
| Hib | 126 | 109 | 310 | 518 | 517 | 550 | 936 | 792 | 390 |
| HBsAg | 88 | 240 | 369 | 2645 | 1784 | 1670 | 4062 | 2308 | 1154 |

Thus lower amounts of MF59 and Al-T still retain good adjuvanticity and can induce higher IgG antibody titers than those induced by unadjuvanted 6-valent antigen formulations. By reducing the amount of adjuvant, while maintaining immunological efficacy, the safety profile of a vaccine can be improved which is particularly important in pediatric settings.

It will be understood that the invention has been described by way of example only and modifications may be made whilst remaining within the scope and spirit of the invention.

TABLE A antigen and $Al^{+++}$ content of various marketed vaccines (per unit dose)

| | D | T | Pa[1] | Hib[2] | IPV[3] | HBsAg | Vol | $Al^{+++}$ |
|---|---|---|---|---|---|---|---|---|
| Pediacel | 15 Lf | 5 Lf | 20/20/3 | 10 | 40/8/32 | — | 0.5 ml | 0.33 mg |
| Pediarix | 25 Lf | 10 Lf | 25/25/8 | — | 40/8/32 | 10 μg | 0.5 ml | ≤0.85 mg |
| Pentacel | 15 Lf | 5 Lf | 20/20/3 | 10 | 40/8/32 | — | 0.5 ml | 0.33 mg |
| Tritan$^x$ HB | ≥30 IU | ≥60 IU | —[4] | — | — | 10 μg | 0.5 ml | 0.63 mg |
| Quinvaxem | ≥30 IU | ≥60 IU | —[4] | 10 | — | 10 μg | 0.5 ml | 0.3 mg |
| Hexavac | 30 Lf | 10 Lf | 25/25/— | 12 | 40/8/32 | 5 μg | 0.5 ml | 0.3 mg |
| Boostrix | 2.5 Lf | 5 Lf | 8/8/2.5 | — | — | — | 0.5 ml | ≤0.39 mg |
| Adacel | 5 Lf | 2 Lf | 2.5/5/3 | — | — | — | 0.5 ml | 0.33 mg |
| Daptacel | 15 Lf | 5 Lf | 10/5/3 | — | — | — | 0.5 ml | 0.33 mg |
| Pentavac | ≥30 IU | ≥40 IU | 25/25/— | 10 | 40/8/32 | — | 0.5 ml | 0.30 mg |
| SII QVac | 20-30 Lf | 5-25 Lf | —[4] | — | — | ≥10 μg | 0.5 ml | ≤1.25 mg |
| TripVacHB | ≥30 IU | ≥60 IU | —[4] | — | — | 10 μg | 0.5 ml | ≤1.25 mg |

Notes:
[1]Pa dose shows amounts of pertussis toxoid, then FHA, then pertactin (μg). Pediacel's, Daptacel's and Adacel's Pa components also contain fimbriae types 2 and 3.
[2]Hib dose shows amount of PRP capsular saccharide (μg).
[3]IPV dose shows amounts of type 1, then type 2, then type 3 (measured in DU).
[4]Tritanrix-HepB, Quinvaxem, Trip Vac HB and SII Q-Vac include whole-cell pertussis antigens

REFERENCES

[1] *Vaccines*. (eds. Plotkin & Orenstein). 4th edition, 2004, ISBN: 0-7216-9688-0.
[2] Francois et al. (2005) *Pediatr Infect Dis J* 24:953-61.
[3] Baylor et al. (2001) *Vaccine* 20 (Supplement 3):518-523
[4] Tamm et al. (2005) *Vaccine* 23:1715-19.
[5] WO2008/028956.
[6] *National Institute for Biological Standards and Control*; Potters Bar, UK. www.nibsc.ac.uk
[7] Sesardic et al. (2001) *Biologicals* 29:107-22.
[8] NIBSC code: 98/560.
[9] Module 1 of WHO's *The immunological basis for immunization series* (Galazka).
[10] NIBSC code: 69/017.
[11] NIBSC code: DIFT.
[12] Sesardic et al. (2002) *Biologicals* 30:49-68.
[13] NIBSC code: 98/552.
[14] NIBSC code: TEFT.
[15] Rappuoli et al. (1991) *TIBTECH* 9:232-238.
[16] Nencioni et al. (1991) *Infect Immun.* 59(2): 625-30.
[17] Ramsay et al. (2001) *Lancet* 357(9251):195-196.
[18] Lindberg (1999) *Vaccine* 17 Suppl 2:S28-36.
[19] Buttery & Moxon (2000) *J R Coll Physicians Lond* 34:163-168.
[20] Ahmad & Chapnick (1999) *Infect Dis Clin North Am* 13:113-133, vii.
[21] Goldblatt (1998) *J. Med. Microbiol.* 47:563-567.
[22] European patent 0477508.
[23] U.S. Pat. No. 5,306,492.
[24] WO98/42721.
[25] *Conjugate Vaccines* (eds. Cruse et al.) ISBN 3805549326, particularly vol. 10:48-114.
[26] Hermanson (1996) *Bioconjugate Techniques* ISBN: 0123423368 or 012342335X.
[27] WO96/40242.
[28] Vanlandschoot et al. (2005) *J Gen Virol* 86:323-31.
[29] WO2007/054820.
[30] WO03/066094.
[31] Liao et al. (2012) *J Infect Dis.* 205:237-43.
[32] Verdijk et al. (2011) *Expert Rev Vaccines.* 10:635-44.
[33] Module 6 of WHO's *The immunological basis for immunization series* (Robertson)
[34] W.H.O. *Tech. Rep. Ser.* 594:51, 1976.
[35] WO03/080678.
[36] Glode et al. (1979) *J Infect Dis* 139:52-56
[37] WO94/05325; U.S. Pat. No. 5,425,946.
[38] Arakere & Frasch (1991) *Infect. Immun.* 59:4349-4356.
[39] Michon et al. (2000) *Dev. Biol.* 103:151-160.
[40] Rubinstein & Stein (1998) *J. Immunol.* 141:4357-4362.
[41] WO2005/033148
[42] WO2005/000347.
[43] WO02/058737.
[44] WO03/007985.
[45] WO2007/000314.
[46] WO2007/000322.
[47] Giuliani et al. (2006) *Proc Natl Acad Sci USA* 103(29):10834-9.
[48] WO99/57280.
[49] Masignani et al. (2003) *J Exp Med* 197:789-799.
[50] Welsch et al. (2004) *J Immunol* 172:5605-15.
[51] Hou et al. (2005) *J Infect Dis* 192(4):580-90.
[52] WO03/063766.
[53] Fletcher et al. (2004) *Infect Immun* 72:2088-2100.
[54] Zhu et al. (2005) *Infect Immun* 73(10):6838-45.
[55] WO2004/048404
[56] Serruto et al. (2010) *PNAS USA* 107:3770-5.
[57] Tettelin et al. (2000) *Science* 287:1809-15.
[58] *WHO Technical Report Series* No. 927, 2005. Pages 64-98.
[59] US-2008/0102498.
[60] US-2006/0228381.
[61] US-2007/0231340.
[62] US-2007/0184072.
[63] US-2006/0228380.
[64] WO2008/143709.

[65] *Research Disclosure*, 453077 (January 2002)
[66] EP-A-0378881.
[67] EP-A-0427347.
[68] WO93/17712
[69] WO94/03208.
[70] WO98/58668.
[71] EP-A-0471177.
[72] WO91/01146
[73] Falugi et al. (2001) *Eur J Immunol* 31:3816-3824.
[74] Baraldo et al. (2004) *Infect Immun* 72(8):4884-7.
[75] EP-A-0594610.
[76] Ruan et al. (1990) *J Immunol* 145:3379-3384.
[77] WO00/56360.
[78] Kuo et al. (1995) *Infect Immun* 63:2706-13.
[79] Michon et al. (1998) *Vaccine.* 16:1732-41.
[80] WO02/091998.
[81] WO01/72337
[82] WO00/61761.
[83] WO00/33882
[84] WO2007/071707
[85] Bethell G. S. et al., *J. Biol. Chem.*, 1979, 254, 2572-4
[86] Hearn M. T. W., *J. Chromatogr.*, 1981, 218, 509-18
[87] WO2007/000343.
[88] *Mol. Immunol.*, 1985, 22, 907-919
[89] EP-A-0208375
[90] WO00/10599
[91] Gever et al., Med. Microbiol. Immunol, 165: 171-288 (1979).
[92] U.S. Pat. No. 4,057,685.
[93] U.S. Pat. Nos. 4,673,574; 4,761,283; 4,808,700.
[94] U.S. Pat. No. 4,459,286.
[95] U.S. Pat. No. 5,204,098
[96] U.S. Pat. No. 4,965,338
[97] U.S. Pat. No. 4,663,160.
[98] US-2007/0184071.
[99] Jodar et al. (2003) *Vaccine* 21:3265-72.

*Vaccine Design: The Subunit and Adjuvant Approach* (eds. Powell & Newman) Plenum Press 1995 (ISBN 0-306-44867-X).

Clausi et al. (2008) *J Pharm Sci* DOI 10.1002/jps.21390.
International patent application PCT/US2011/050231.
U.S. patent application 61/316,551.
U.S. patent application 61/379,126.
WO2011/027222.
WO2011/024072.
WO2010/144734.
WO90/14837.

Podda & Del Giudice (2003) *Expert Rev Vaccines* 2:197-203.
Podda (2001) *Vaccine* 19: 2673-2680.

*Vaccine Adjuvants: Preparation Methods and Research Protocols* (Volume 42 of *Methods in Molecular Medicine* series). ISBN: 1-59259-083-7. Ed. O'Hagan.

WO2008/043774.
Allison & Byars (1992) *Res Immunol* 143:519-25.
Hariharan et al. (1995) *Cancer Res* 55:3486-9.
US-2007/014805.
WO2007/080308.
WO95/11700.
U.S. Pat. No. 6,080,725.
WO2005/097181.
WO2006/113373.
U.S. Pat. No. 6,630,161.
Nony et al. (2001) *Vaccine* 27:3645-51.
WO01/41800.
Dupuis et al. (1999) *Vaccine* 18:434-9.
*Immunopotentiators in Modern Vaccines* (2006) Schijns and O'Hagan (eds.) ISBN: 0-12-088403-8.

The invention claimed is:

1. An immunogenic composition in a unit dose form for administration to a patient comprising (i) a diphtheria toxoid, a tetanus toxoid, and an acellular pertussis antigen which contains a pertussis toxoid, (ii) an aluminium salt adjuvant, wherein the amount of $Al^{+++}$ in the unit dose is less than 0.2 mg, and (iii) a toll-like receptor 7 (TLR 7) agonist, wherein at least 50% (by weight) of the TLR 7 agonist is adsorbed to the aluminium salt adjuvant.

2. The composition of claim 1, further comprising one or more of (i) a Hib conjugate, (ii) a hepatitis B virus surface antigen, and/or (iii) an inactivated poliovirus antigen.

3. An immunogenic composition in a unit dose form for administration to a patient comprising (i) a low dose of each of a diphtheria toxoid, a tetanus toxoid, and a pertussis toxoid, (ii) an aluminium salt adjuvant, wherein the amount of $Al^{+++}$ in the unit dose is less than 0.2 mg, and (iii) a TLR 7 agonist, wherein at least 50% (by weight) of the TLR 7 agonist is adsorbed to the aluminium salt adjuvant.

4. The composition of claim 3, wherein the composition has ≤8 Lf/ml diphtheria toxoid.

5. The composition of claim 3, wherein the composition has ≤3.5 Lf/ml tetanus toxoid.

6. The composition of claim 3, wherein the acellular pertussis antigen has ≤5 µg/ml pertussis toxoid.

7. The composition of claim 3, further comprising a low dose of an *H. influenzae* type b ("Hib") conjugate.

8. The composition of claim 7, wherein the composition has ≤5 µg/ml Hib saccharide.

9. The composition of claim 3, further comprising a low dose of surface antigen of the hepatitis B virus ("HBsAg").

10. The composition of claim 9, wherein the composition has ≤5 µg/ml HBsAg.

11. The composition of claim 3, further comprising a low dose of inactivated poliovirus.

12. The composition of claim 11, wherein the composition has (i) ≤20 DU/ml type 1 poliovirus and/or (ii) ≤4 DU/ml type 2 poliovirus and/or (iii) ≤16 DU/ml type 3 poliovirus.

13. The composition of claim 3, wherein the aluminium salt adjuvant is (i) an aluminium hydroxide adjuvant or (ii) an aluminium phosphate adjuvant or (iii) a mixture of an aluminium hydroxide adjuvant and an aluminium phosphate adjuvant.

14. The composition of claim 3, wherein the aluminium salt adjuvant is an aluminium hydroxide adjuvant.

15. The composition of claim 1, wherein the at least 50% (by weight) of the TLR agonist adsorbed to the aluminium salt adjuvant is in a stable complex with the aluminium salt adjuvant.

* * * * *